US010336539B2

(12) United States Patent
Caveney et al.

(10) Patent No.: US 10,336,539 B2
(45) Date of Patent: Jul. 2, 2019

(54) AUTOMATED CRYOGENIC STORAGE SYSTEM

(71) Applicant: Brooks Automation, Inc., Chelmsford, MA (US)

(72) Inventors: Robert T. Caveney, Nashua, NH (US); Frank Hunt, Shrewsbury, MA (US); Lingchen Sun, Milford, MA (US); Julian D. Warhurst, Portsmouth, RI (US); Bruce S. Zandi, Lexington, MA (US); Anthony C. Bonora, Portola Valley, CA (US)

(73) Assignee: Brooks Automation, Inc., Chelmsford, MA (US)

( * ) Notice: Subject to any disclaimer, the term of this patent is extended or adjusted under 35 U.S.C. 154(b) by 354 days.

(21) Appl. No.: 15/085,431

(22) Filed: Mar. 30, 2016

(65) Prior Publication Data
US 2016/0288999 A1 Oct. 6, 2016

Related U.S. Application Data

(60) Provisional application No. 62/140,157, filed on Mar. 30, 2015.

(51) Int. Cl.
B65G 1/04 (2006.01)
B65G 1/06 (2006.01)
(Continued)

(52) U.S. Cl.
CPC ........... B65G 1/045 (2013.01); B65G 1/0464 (2013.01); B65G 1/06 (2013.01); B65G 1/10 (2013.01);
(Continued)

(58) Field of Classification Search
CPC ........ B65G 1/045; B65G 1/0464; B65G 1/06; B65G 1/10; F25D 3/105; F25D 3/11;
(Continued)

(56) References Cited

U.S. PATENT DOCUMENTS 5,233,844 A 8/1993 Knippscheer et al.
5,921,102 A 7/1999 Vago
(Continued)

FOREIGN PATENT DOCUMENTS

CH 114763 A 4/1926
EP 2492663 A2 2/2012
(Continued)

OTHER PUBLICATIONS

Translation of EP 2492663A2 (Year: 2012).*
(Continued)

Primary Examiner — Elizabeth J Martin
(74) Attorney, Agent, or Firm — Hamilton, Brook, Smith & Reynolds, P.C.

(57) ABSTRACT

An automated cryogenic storage system includes a freezer and an automation system to provide automated transfer of samples to and from the freezer. The freezer includes a bearing and a drive shaft though the freezer, the drive shaft being coupled to a rack carrier inside the freezer and adapted to be coupled to a motor. The automation module includes a rack puller that is automatically positioned above an access port of the freezer. The rack puller engages with a sample rack within the freezer, and elevates the rack into an insulating sleeve external to the freezer. From the insulating sleeve, samples can be added to and removed from the sample rack before it is returned to the freezer.

27 Claims, 36 Drawing Sheets

(51) Int. Cl.

| | |
|---|---|
| *B65G 1/10* | (2006.01) |
| *F25D 3/10* | (2006.01) |
| *F25D 21/02* | (2006.01) |
| *F25D 21/04* | (2006.01) |
| *F25D 25/02* | (2006.01) |
| *F25D 29/00* | (2006.01) |
| *F25D 3/11* | (2006.01) |
| *F25D 25/04* | (2006.01) |

(52) U.S. Cl.
CPC ............... *F25D 3/105* (2013.01); *F25D 3/11* (2013.01); *F25D 21/02* (2013.01); *F25D 21/04* (2013.01); *F25D 25/02* (2013.01); *F25D 29/001* (2013.01); *F25D 25/04* (2013.01); *F25D 2400/38* (2013.01)

(58) Field of Classification Search
CPC .... F25D 29/011; F25D 25/04; F25D 2400/38; G01N 1/42; A01N 1/0257
See application file for complete search history.

(56) References Cited

U.S. PATENT DOCUMENTS

| | | | |
|---|---|---|---|
| 6,393,847 B1 | 5/2002 | Brooks et al. | |
| 2003/0233842 A1 | 12/2003 | Junca et al. | |
| 2010/0253190 A1* | 10/2010 | Li | 1/242 |
| 2012/0134898 A1 | 5/2012 | Malin | |
| 2016/0289000 A1 | 10/2016 | Caveney et al. | |

FOREIGN PATENT DOCUMENTS

| | | |
|---|---|---|
| EP | 2492663 A2 | 8/2012 |
| WO | WO 2016/160984 A1 | 10/2016 |
| WO | WO 2016/160986 A2 | 10/2016 |

OTHER PUBLICATIONS

Invitation to Pay Additional Fees including Communication Relating to Results of Partial International Search for Int'l Application No. PCT/US2016/025002, "Automated Cryogenic Storage System," dated Jul. 11, 2016.

Invitation to Pay Additional Fees including Communication Relating to Results of Partial International Search for Int'l Application No. PCT/US2016/025004, "Cryogenic Freezer," dated Jul. 15, 2016.

Notification and Transmittal of the International Search Report and the Written Opinion of the International Searching Authority for Int'l Application No. PCT/US2016/025002, "Automated Cryogenic Storage System," dated Sep. 1, 2016.

Notification and Transmittal of the International Search Report and the Written Opinion of the International Searching Authority for Int'l Application No. PCT/US2016/025004, "Cryogenic Freezer," dated Sep. 30, 2016.

Notification Concerning Transmittal of Int'l Preliminary Report on Patentability for Int'l Application No. PCT/US2016/025004, "Cryogenic Freezer," dated Oct. 12, 2017.

Notification Concerning Transmittal of Int'l Preliminary Report on Patentability for Int'l Application No. PCT/US2016/025002, "Automated Cryogenic Storage System," dated Oct. 12, 2017.

Office Action, U.S. Appl. No. 15/085,630, "Cryogenic Freezer" dated Mar. 29, 2019.

* cited by examiner

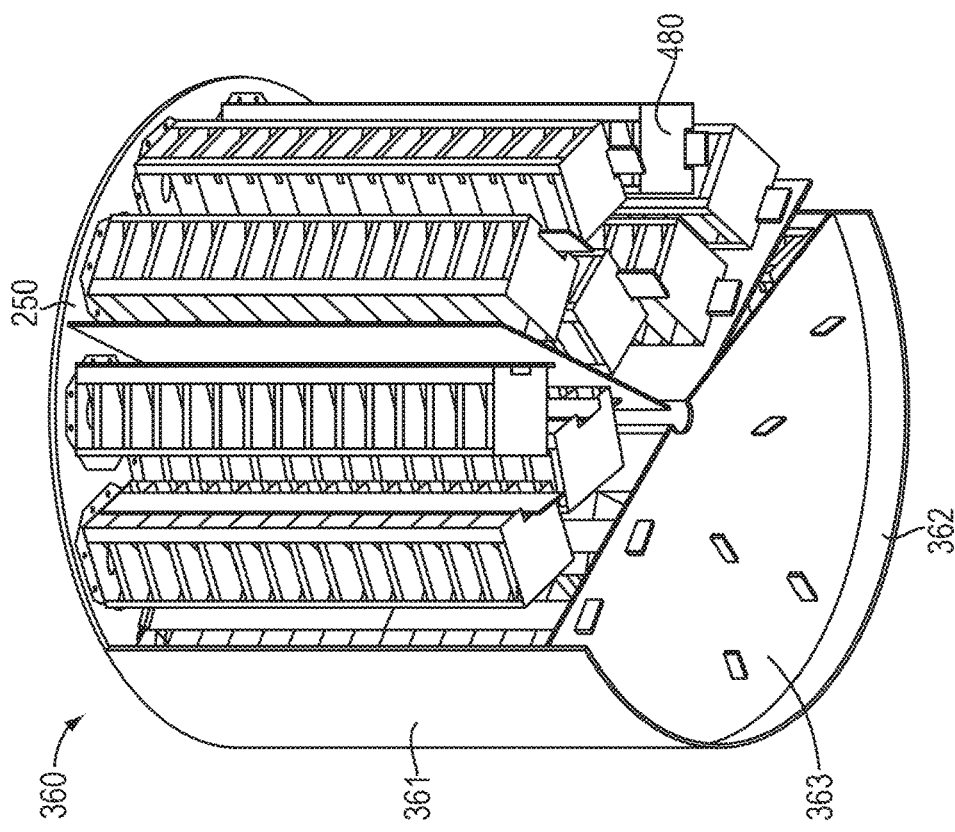
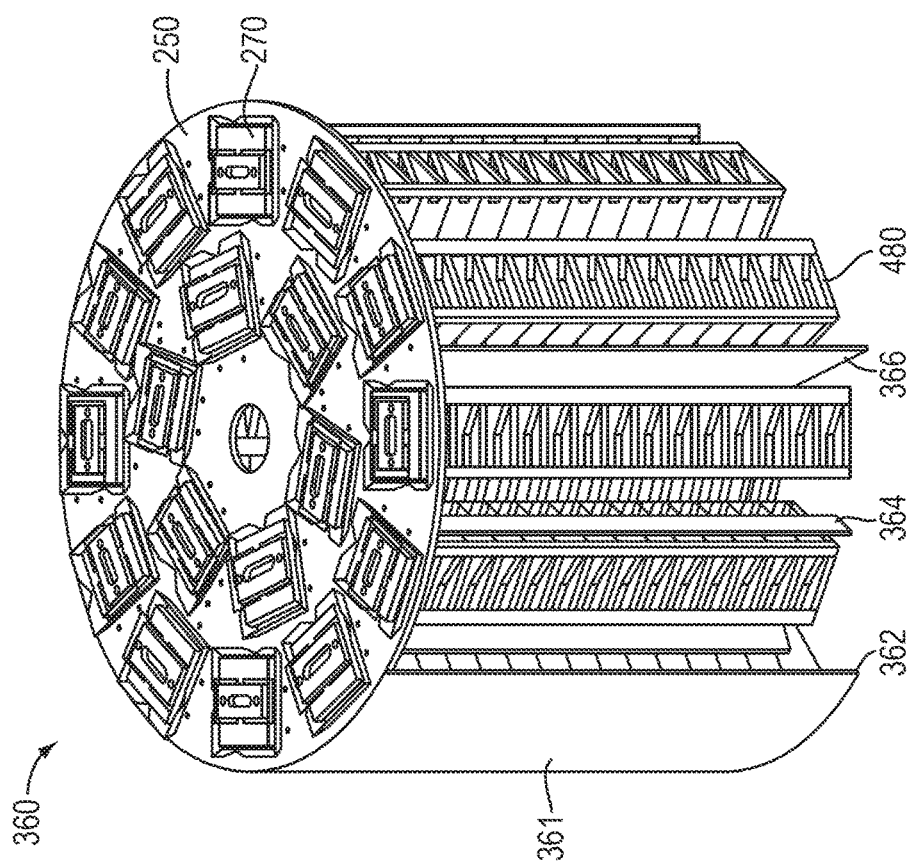

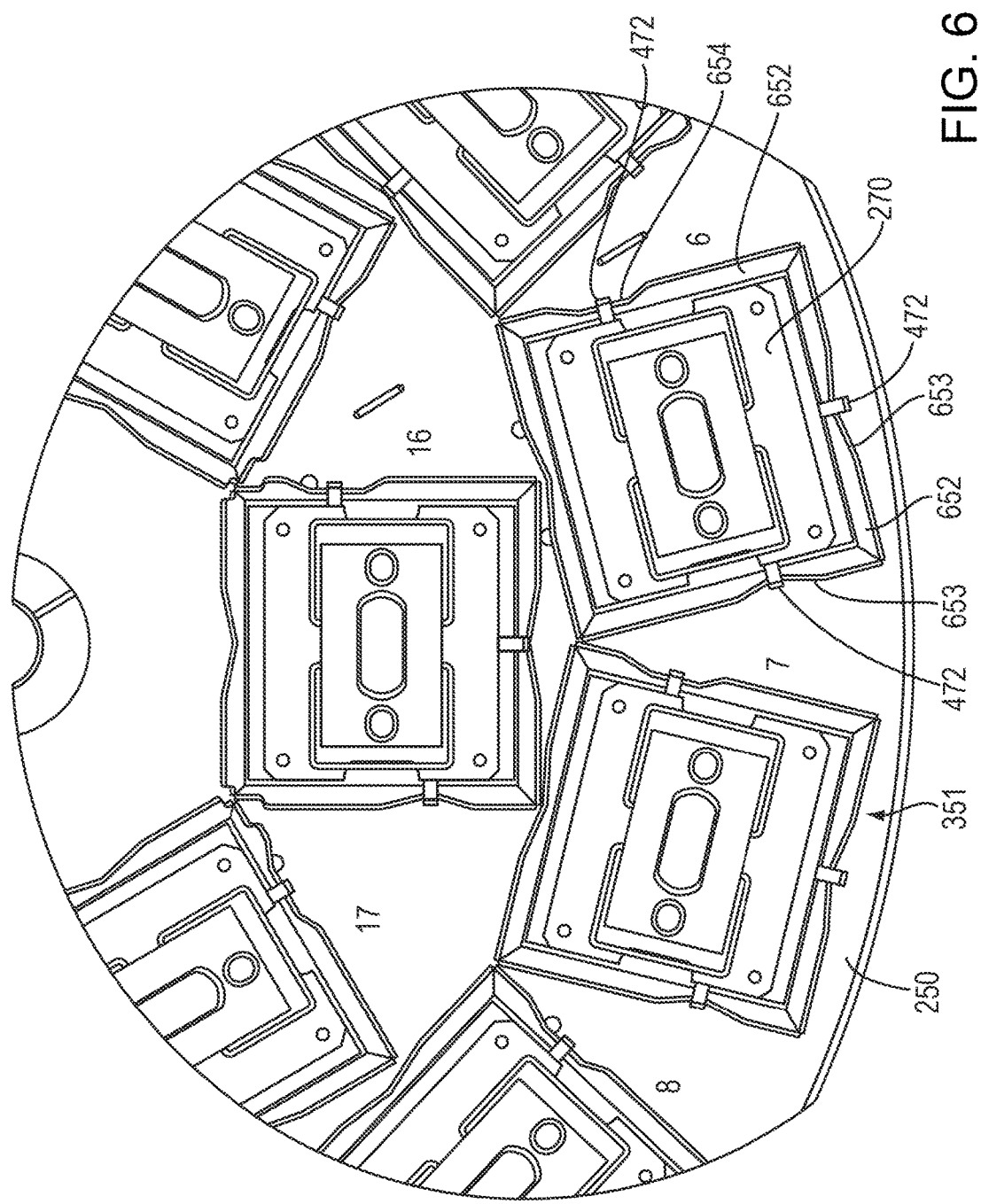

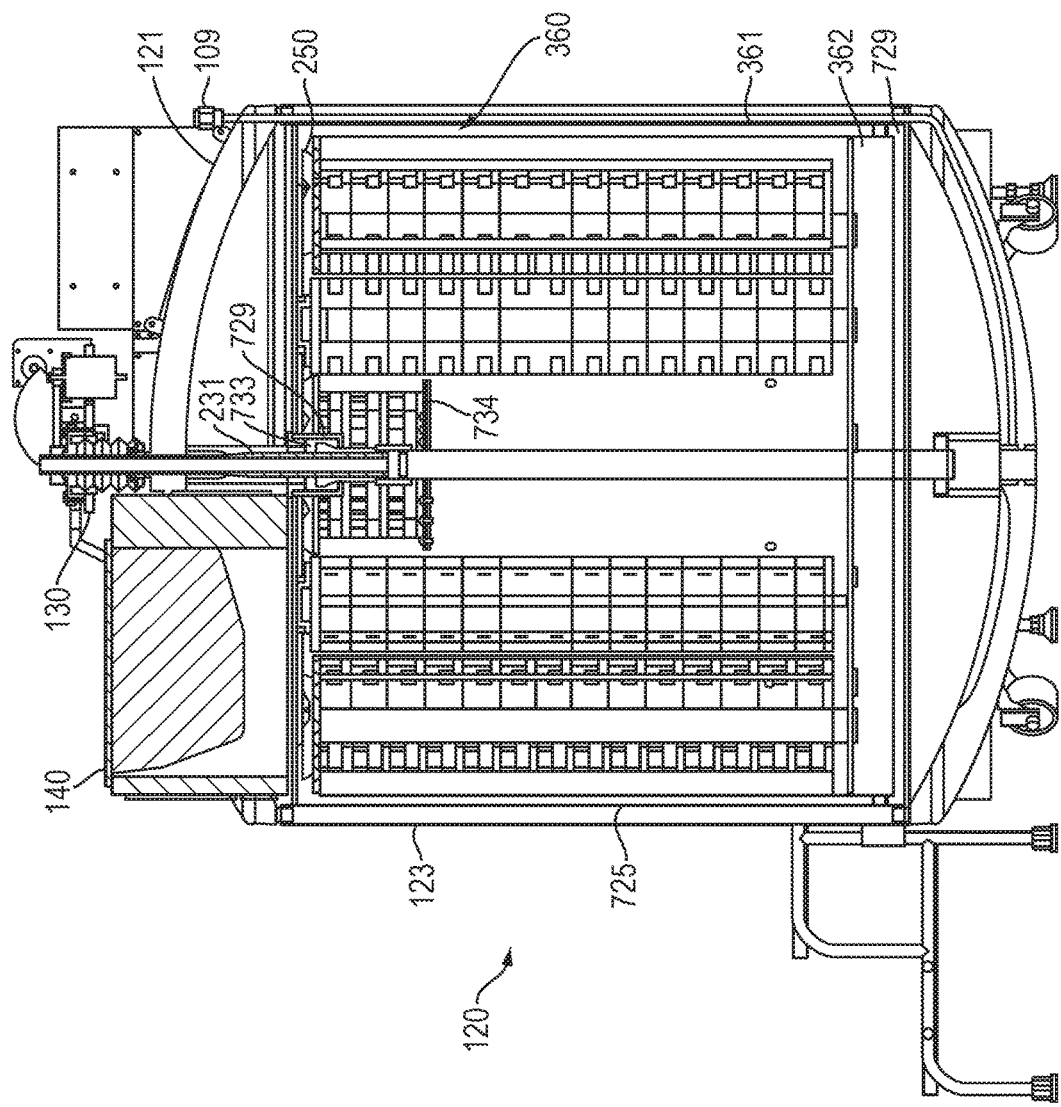

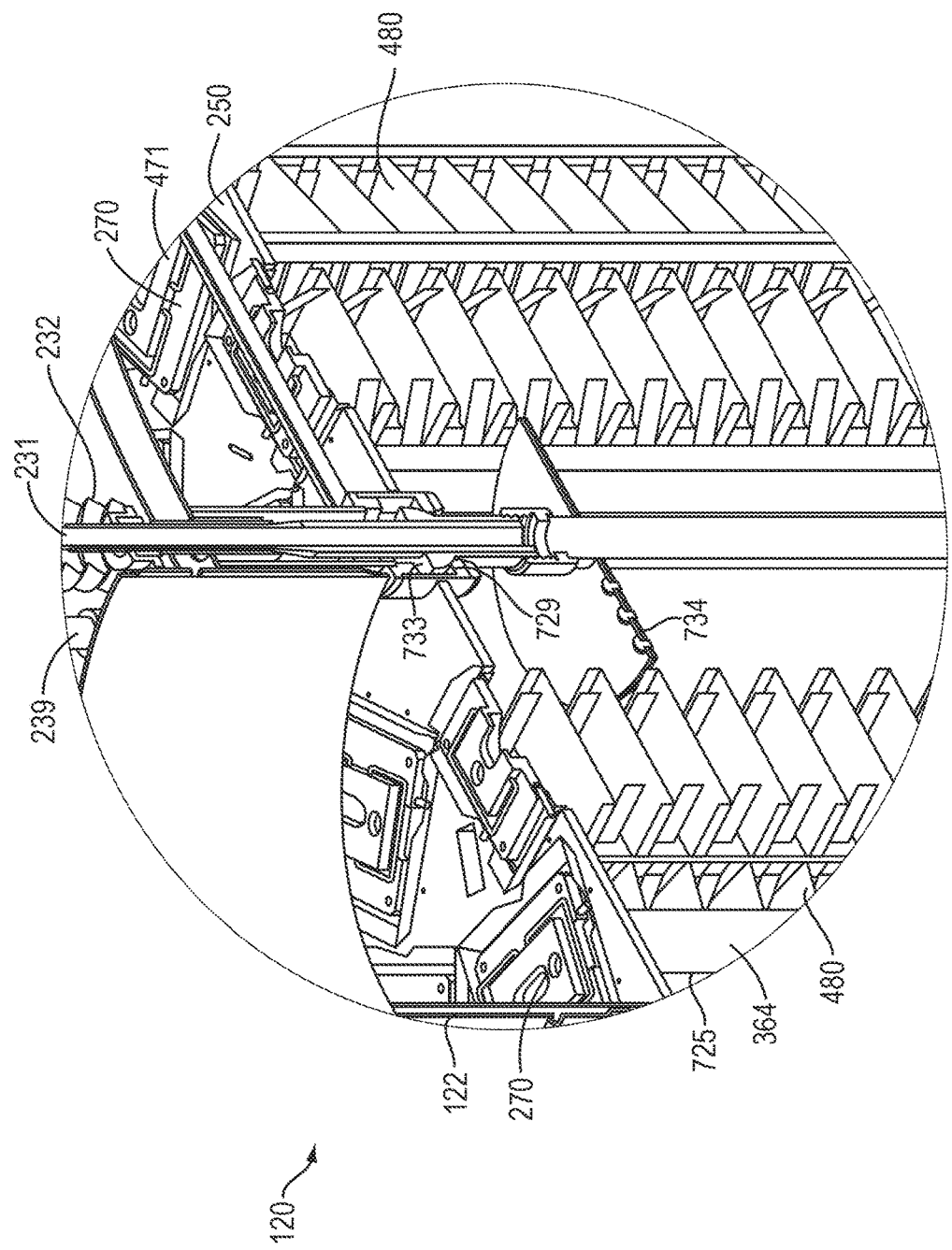

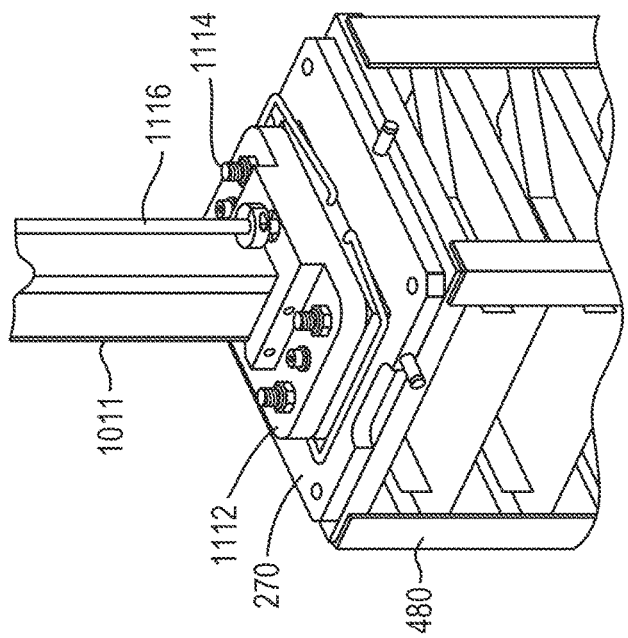
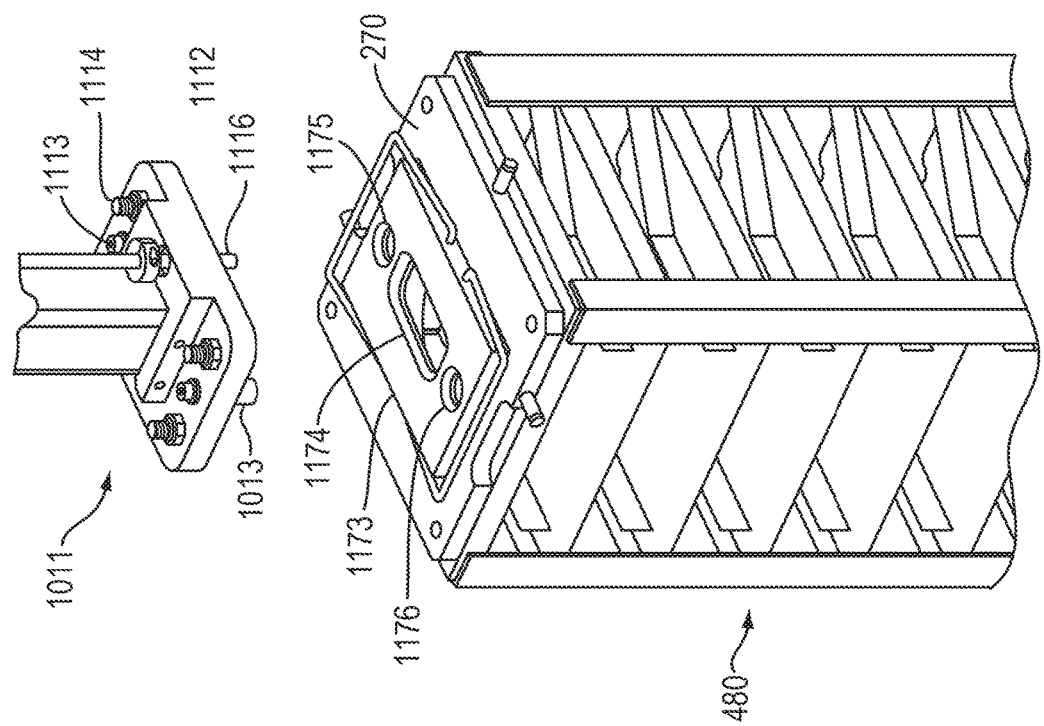

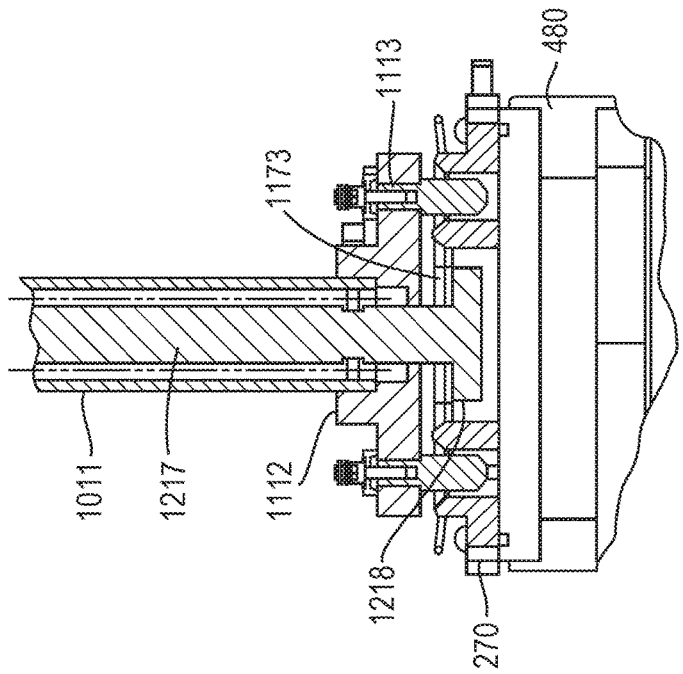
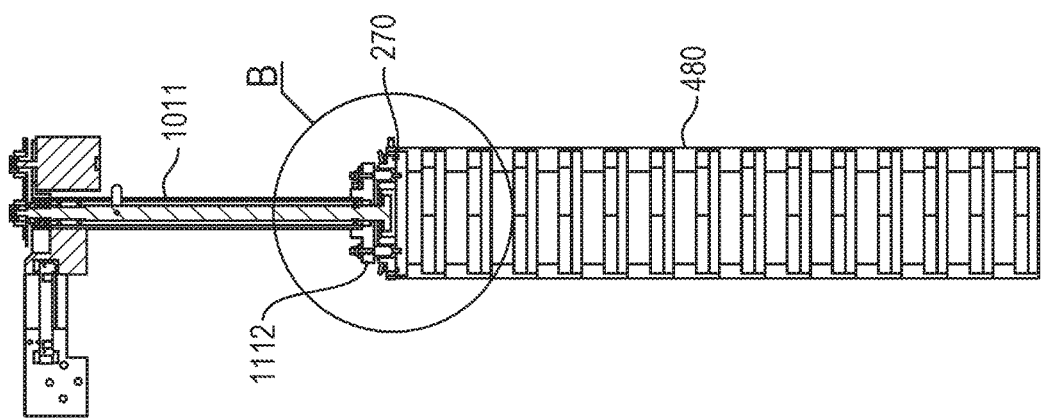

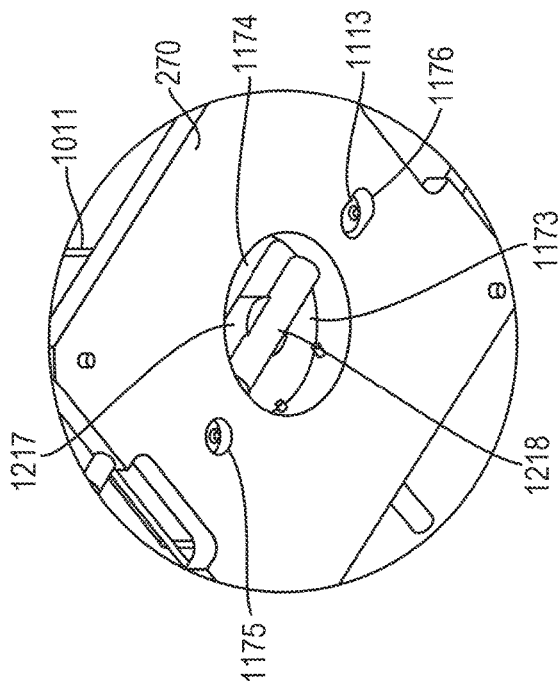
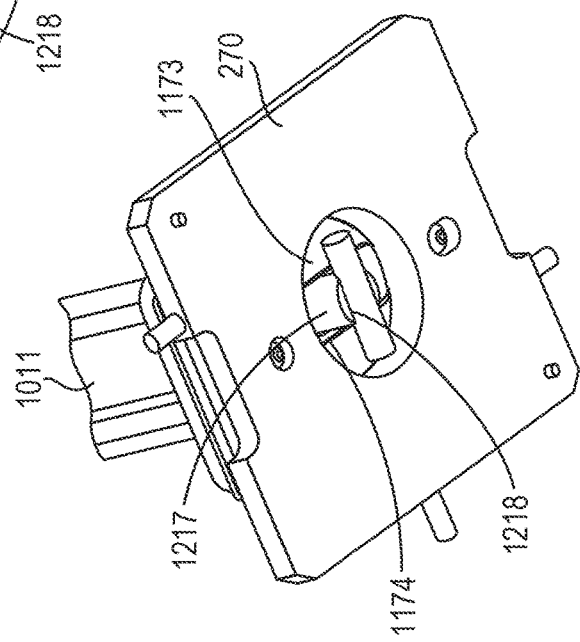
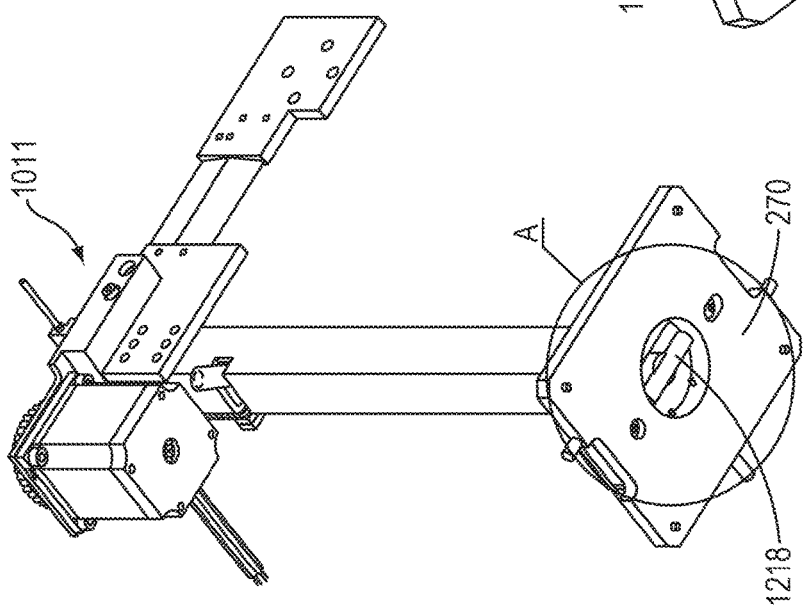
FIG. 13B
FIG. 13C
FIG. 13A

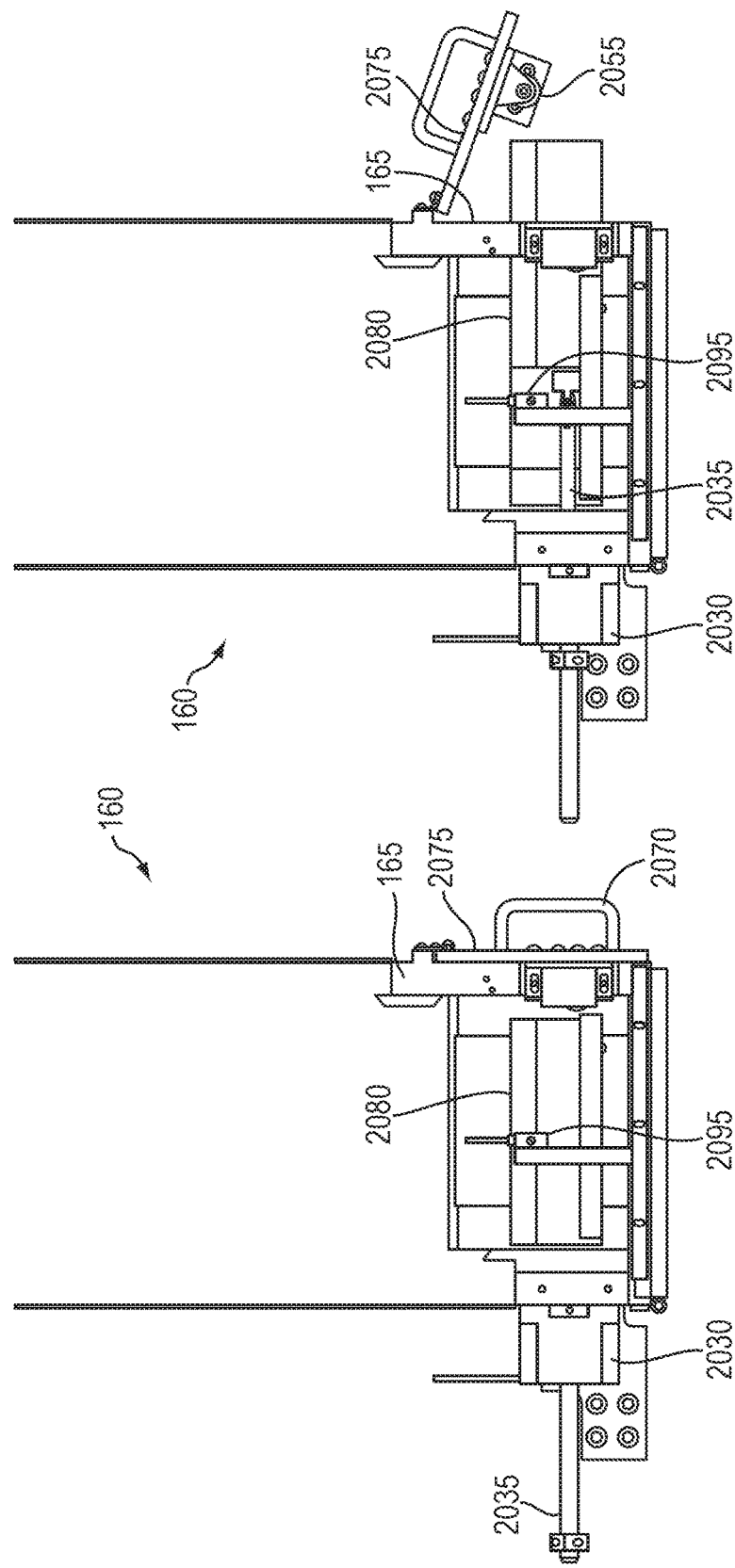

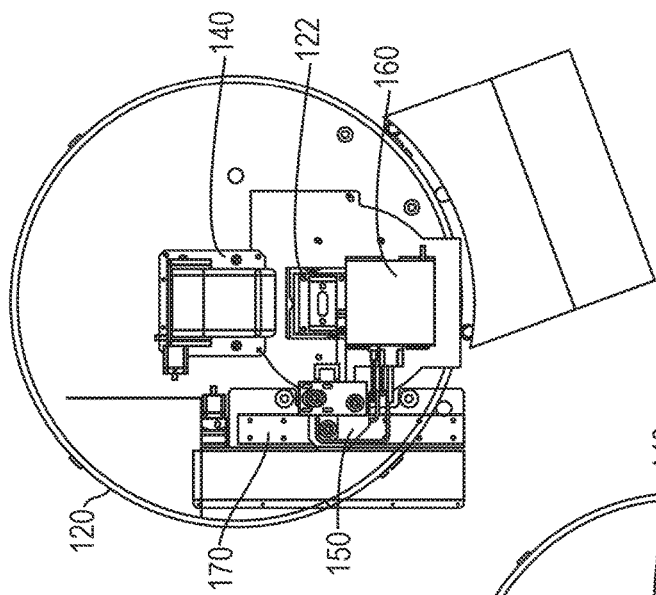
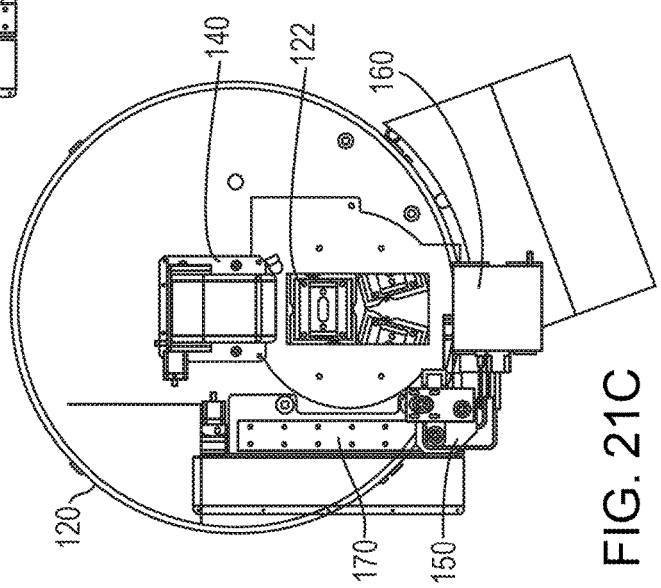
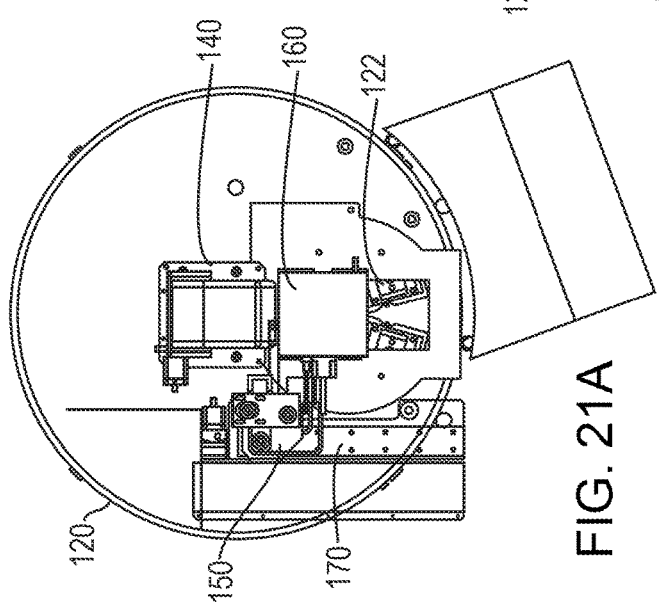

AUTOMATED CRYOGENIC STORAGE SYSTEM

RELATED APPLICATIONS

This application claims the benefit of U.S. Provisional Application No. 62/140,157, filed on Mar. 30, 2015. The entire teachings of the above application is incorporated herein by reference.

BACKGROUND

Cryopreservation is a process essential to maintaining the integrity of biological substances over extended periods of storage. At sufficiently low temperatures, all chemical processes and biological functions of such substances are effectively halted, allowing them to be stored safely over nearly any length of time. A cryogenic storage freezer enables such storage by providing an insulated and controlled cryogenic environment to accommodate a number of biological or other samples. In typical storage freezers, samples are loaded into racks or trays, each of which hold several samples. The racks or trays are manually removed from the cryogenic environment of the freezer, presenting the rack or tray to a user for removing samples from, or adding samples to, the storage freezer.

SUMMARY OF THE INVENTION

Example embodiments of the disclosure provide a cryogenic storage system comprising a freezer and an automated retrieval system. The freezer stores a plurality of sample racks in a cryogenic environment, and includes a door enabling access to the cryogenic environment through a port at the top portion of the freezer. The retrieval system may include a drive system, an insulating sleeve and a rack puller. The drive system may be mounted to the top portion of the freezer, and operates to rotate the sample racks to align a selected one of the sample racks with the port. The insulating sleeve houses the selected sample rack above the port, and includes a sleeve port for enabling a user to access a selected sample box from the sample rack. The rack puller may be mounted to the top portion of the freezer and operates to engage the selected sample rack to elevate the rack through the freezer port and into the insulating sleeve.

In further embodiments, the freezer may further include a rack carrier configured to suspend each of the plurality of sample racks by a respective rack top portion. The rack carrier may include a rack mount having multiple openings, the rack mount suspending each of the plurality of sample racks at a respective one of the plurality of openings. Each of the openings may include a guide extending vertically from a top surface of the rack mount, the guide adapted to center a respective sample rack within the opening. The drive system may engage with a shaft to rotate the rack carrier. In such a configuration, the rack carrier may further include a rack mount, the shaft suspending the rack carrier substantially via the rack mount. The rack carrier may also include a plurality of rails each positioned adjacent to a respective one of the plurality of sample racks.

In still further embodiments, each of the plurality of racks may include a guideplate at a top portion of the rack, the guideplate including at least one formation for engaging with the rack puller. The retrieval system may also include an actuator for automatically opening and closing the door. The system may further include a mount configured to mount one or both of the insulating sleeve and rack puller to the top portion of the freezer. The mount may enable the insulating sleeve to be manually repositioned away from the port to enable manual access to the plurality of sample racks. The mount may further include a manual release enabling the manual reposition independent of a powered status of the retrieval system.

In yet still further embodiments, the rack puller may operate to elevate the selected sample rack to a position aligning the selected sample box to the sleeve port. The insulating sleeve may also prevent access to other sample boxes of the selected sample rack when the selected sample box is aligned with the sleeve port. The insulating sleeve may further include an inlet to channel an expellant gas into the insulating sleeve. The retrieval system may channel the expellant gas into the insulating sleeve prior to elevating the selected one of the sample racks into the insulating sleeve.

In still further embodiments, the system may include a conveyor that operates to automatically move the insulating sleeve and rack puller toward the port. The insulating sleeve and rack puller may be mounted to the top surface of the freezer by the conveyor. Further, the freezer may be a cryogenic liquid-cooled, vacuum-insulated vessel.

Still further embodiments may include a method of cryogenic storage. A plurality of sample racks may be stored in a freezer maintaining a cryogenic environment. The sample racks may be automatically rotated to align a selected one of the sample racks with a port through a top portion of the freezer. A door corresponding to the port may be automatically opened, and the selected sample rack may be automatically engaged via a gripping device. The selected sample rack may then be elevated automatically, via the gripping device, through the port and through an insulating sleeve external to the freezer. A selected sample box of the selected sample rack may be aligned automatically to a sleeve port of the insulating sleeve to enable a user to access the selected sample box.

Yet still further embodiments may include a method of retrieving samples from a cryogenic environment. An uncontrolled environment may be maintained within an insulating sleeve over a freezer. An expellant gas may be channeled into the insulating sleeve. A sample rack may be elevated through a port of the freezer into the insulating sleeve to enable access to at least one sample in the rack through a port of the insulating sleeve. The sample rack may then be lowered from the insulating sleeve into the freezer. The insulating sleeve may be mounted to a top portion of the freezer. Further, the uncontrolled environment may be reintroduced within the insulating sleeve following the lowering of the sample rack.

In further embodiments, a cryogenic storage device may comprise a freezer containing a cryogenic environment and a port enabling access to the cryogenic environment through a top portion of the freezer. A rotating rack carrier inside the freezer includes a plurality of rack-mounting features configured to accept a sample storage racks. The rack carrier secures the sample storage racks by an interface member coupled to each upper end of the sample storage racks. The rack carrier enables the sample storage racks to be removed manually through the port and the rack carrier can be reconfigured to be rotated by a motor and allow the sample storage racks to be retrieved by a retrieval module coupled with the freezer. The freezer includes a bearing having a rotating bearing member coupled with the rack carrier and a stationary race coupled to the freezer. For manual operation, the bearing is configured to support the rack carrier when the stationary race is coupled with the rotating bearing member. The freezer also includes a shaft interface providing a drive shaft though at least a portion of the freezer. To enable automated rotation, the drive shaft has an exterior portion configured to be coupled to a motor and an interior portion coupled to the rack carrier. To reconfigure the freezer, the drive shaft enables vertical translation of the rack carrier to decouple the rotating bearing member from the stationary race. The drive shaft is configured to support the rack carrier when the rotating bearing member is decoupled from the stationary race.

In some embodiments, the sample storage racks hang from the rack-mounting features by the interface members. The drive shaft coupling with the motor may lift the rotating bearing off of the stationary race and enables the motor to support and level the rack carrier via the drive shaft.

The cryogenic storage device may include a manual rotation configuration and an automated rotation configuration where the rack carrier rests on the rotating bearing in the manual rotation configuration and the rack carrier hangs from the drive shaft coupled to the motor in the automated rotation configuration. Coupling the drive shaft to the motor lifts the rack carrier off of the rotating bearing and transitions the configurable cryogenic storage device from the manual rotation configuration to the automated rotation configuration. In some embodiments, in the automated rotation configuration, the motor supports the weight of the rack carrier via the drive shaft. The rack-mounting features may be coupled to the interior end of the dive shaft, the rack-mounting features supporting the rack carrier.

In some embodiments, the exterior end of the drive shaft includes threads adapted to screw the drive shaft into corresponding threads of the motor assembly, and threading the drive shaft into the corresponding threads of the motor assembly lifts the rack carrier off the bearing.

In some embodiments, the freezer further includes a volume of cryogenic liquid with a lower portion the rack carrier extending into the volume of cryogenic liquid. The top plate being in thermal contact with the lower portion enables the rack-mounting features to conduct heat into the volume of cryogenic liquid and form a cooled thermal mass above the sample storage racks.

In some embodiments, each of the interface members includes through holes adapted to accept locating pins, the through holes enabling any frost on the interface member to be pushed through the through holes by the locating pins.

In some embodiments, the rotating bearing may be a spherical bearing comprising a spherical feature and a corresponding running surface surrounding a portion of the surface of the spherical feature, the spherical feature may be integrated into the drive shaft and the corresponding running surface may be coupled to the freezer, and coupling the drive shaft to the motor lifts and separates the spherical feature from the corresponding running surface.

In some embodiments, an exterior surface of the top portion of the freezer includes mounting points adapted to secure the motor to the freezer. The mounting features support the weight of the motor and the rack carrier when the configurable cryogenic storage device is in the automated configuration. The mounting points may enable leveling of the motor and rack carrier.

In some embodiments an exterior surface of the top portion of the freezer includes at least one mounting feature adapted to secure a retrieval module, the retrieval module is configured to access the freezer and engage a selected one of the plurality of sample storage racks in the rack carrier via the interface member and elevate the selected one of the sample storage racks through the door and into the retrieval module.

In some embodiments, each interface member includes three locating pins protruding from at least two opposing sides of the interface member, and each rack-mounting feature, which may be integrated into a top plate further comprises corresponding grooves adapted to accept each locating pin of the interface member. In some embodiments, each corresponding opening of the plurality of rack-mounting feature includes guide fins surrounding the corresponding opening to guide a bottom end of one of the plurality of sample storage racks when the sample storage rack is lowered through the rack-mounting features or the corresponding openings in the top plate having the rack-mounting features. In some embodiments, the guide fins surrounding each corresponding opening include the corresponding grooves. When accepted, the three locating pins and corresponding grooves constrain the interface member and the attached sample storage rack in three dimensions.

Another example embodiment of the present invention is a cryogenic storage device having a freezer and a door enabling access to the cryogenic environment through a top portion of the freezer. The freezer includes a rotating bearing and a shaft interface providing a drive shaft though the freezer, the drive shaft having an exterior end adapted to be coupled to a motor and an interior end inside the freezer, a volume of cryogenic fluid inside the freezer, the volume of cryogenic fluid pooling on a bottom surface of the inside of the freezer, and a rack carrier positioned inside of the freezer holding a plurality of sample storage racks. The rack carrier includes a top plate with a plurality of rack-mounting features, with each of the rack-mounting features adapted to accept a sample storage rack through a corresponding opening in the top plate. A lower portion the rack carrier extends into the volume of cryogenic liquid. The top plate is in thermal contract with the cryogenic fluid via the lower portion of the rack carrier and the top plate conducts heat into the volume of cryogenic liquid to form a thermal mass above the sample storage racks.

Yet another example embodiment of the present invention is a method of converting a manual operation freezer into an automated operation freezer, the method includes, providing a freezer having a drive shaft though a top portion of the freezer and a rack carrier positioned inside of the freezer, the rack carrier resting on a bearing and adapted to be supported by the drive shaft, attaching a motor to an exterior surface of the top portion of the freezer, lifting the rack carrier off the rotating bearing using the drive shaft, the lifting causing the rack carrier to be supported by the drive shaft, and securing the drive shaft to the motor.

In some embodiments, the drive shaft includes a threaded end, and lifting the rack carrier off the rotating bearing using the drive shaft may include threading the threaded end of the drive shaft into corresponding threads of the motor assembly, thus lifting the rack carrier off of the rotating bearing. Threading the threaded end of the drive shaft onto the motor assembly may include manually rotating the rack carrier through a door in the top portion of the freezer.

Further embodiments include a device for engaging with a sample rack, comprising a bracket, a gripping module, and a shaft extending between the bracket and the gripping module. The bracket may be configured to be coupled with an automated retrieval system, and the gripping module may be configured to engage with a mounting surface of a sample rack. The device may also include at least one moisture diverter configured to direct moisture away from the gripping module. The gripping module may further include a latch configured to lock selectively with the mounting surface, and the latch may be configured to be controlled via rotation of a rod located within the shaft. A seal may encompass the rod at a location within the shaft and adjacent to a top portion of the gripping module. The moisture diverter includes a drip shield including angled leaves configured direct moisture away from an underside of the gripping module. The gripping module may also include at least one spacer pin extending downward from a bottom surface of the gripping module, where the spacer pin is configured to contact the mounting surface of the sample rack when the gripping module is engaged with the mounting surface.

Still further embodiments include a method of engaging with a sample rack. A gripping module is lowered toward a mounting surface of a sample rack until a spacer of the gripping module contacts the mounting surface, a bottom surface of the gripping module being isolated from the mounting surface. The gripping module is then engaged to latch with the mounting surface. The gripping module, with the sample rack, may then be raised. The spacer may include a spacer pin.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIGS. 5A-B are illustrations of a rack carrier and top plate with the top plate securing a plurality of sample storage racks by their respective interface members in accordance with aspects of the disclosed embodiment.

FIG. 6 is an illustration of the top plate of and integrated rack-mounting features of FIG. 5A showing interface between the locating pins on the interface members and the rack-mounting features in accordance with aspects of the disclosed embodiment.

FIG. 7 is a cross-section illustration of a cryogenic storage freezer with a rack carrier coupled to a drive shaft and motor in accordance with aspects of the disclosed embodiment.

FIG. 8 is an isometric view of a cross-section of a cryogenic storage freezer with a rack carrier configured for manual operation in accordance with aspects of the disclosed embodiment.

FIGS. 11A-B are illustrations of a gripper assembly of a retrieval module mating with an interface member of a sample storage rack in accordance with aspects of the disclosed embodiment.

FIGS. 12A-B are cross-section illustrations of a gripping assembly mated to an interface member of a sample storage rack of in accordance with aspects of the disclosed embodiment.

FIGS. 13A-C are illustrations of the latch of a gripping assembly mating with an interface member of in accordance with aspects of the disclosed embodiment.

FIGS. 20A-D illustrate an insulating sleeve in one embodiment.

FIGS. 21A-C illustrate a conveyor and operation thereof in one embodiment.

DETAILED DESCRIPTION OF THE INVENTION

A description of example embodiments of the invention follows.

Figure 1:
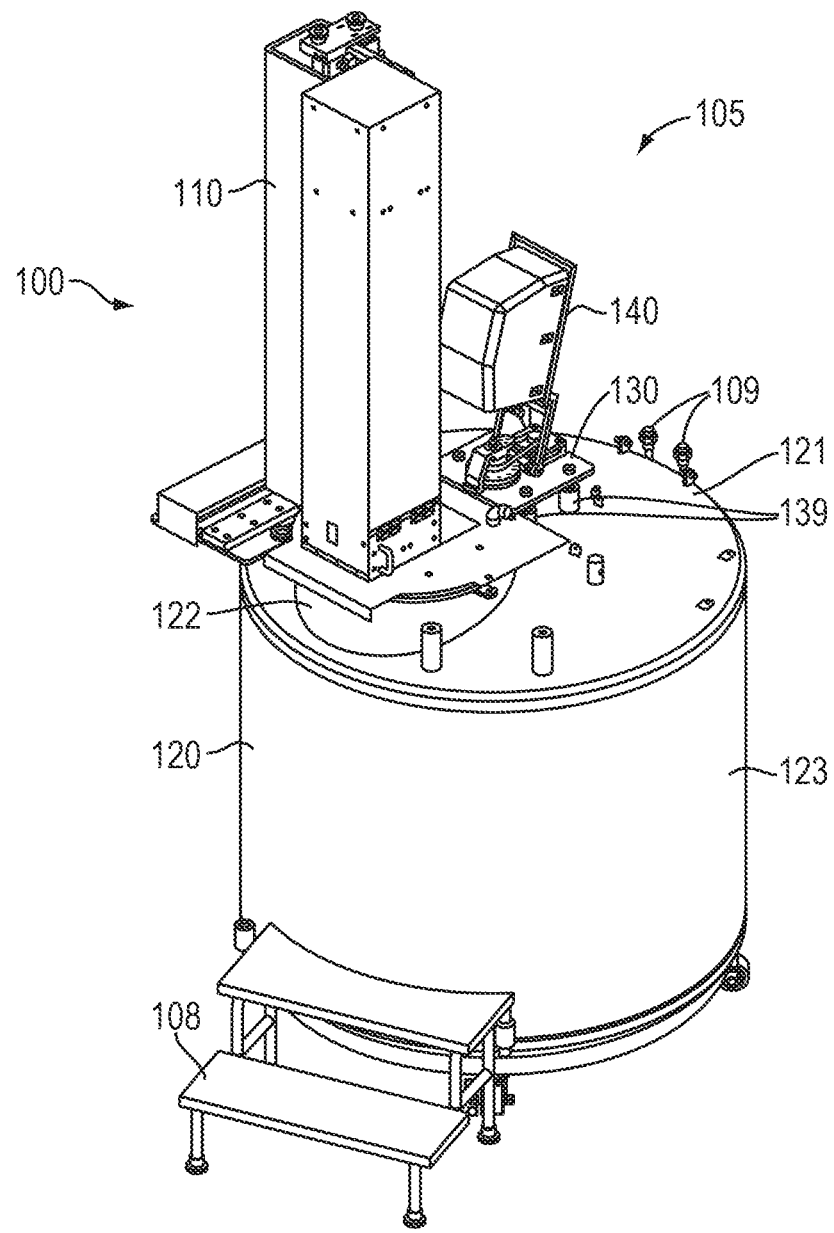
FIG. 1 is an illustration of a configurable cryogenic storage device in accordance with aspects of the disclosed embodiment.

FIG. 1 is an illustration of a configurable cryogenic storage device in accordance with aspects of the disclosed embodiment. FIG. 1 shows a configurable cryogenic storage device 100 comprising a freezer 120 and an automation system 105 having a retrieval module 110, a rotation motor assembly 130, and a freezer door 140 mounted to the freezer 120. The freezer 120 includes a freezer cover 121 and an external wall 123. In the illustrated embodiments, freezer 120 is a cylindrical vessel; however, the freezer can have any shape such as, for example, a rectangular box. In some preferred embodiments, freezer 120 includes an external wall or shell separated from an inner wall or shell by a vacuum insulated space (e.g., a Dewar vessel). The exterior of the freezer cover 121 includes motor mounts 139 which enable attachment of the motor assembly 130. Cryogenic refrigerant ports 109 ingress and egress to carry a cryogenic refrigerant such as, for example, liquid nitrogen, to and from an inner chamber of the freezer 120. Finally, optional stairs 108 positioned in front of the freezer 120 and near the retrieval module 110 allow an operator to access the retrieval module 110.

In operation, the freezer 120 maintains a cryogenic environment in an inner chamber with a plurality of sample storage racks (not shown). The retrieval module 110 accesses the inner chamber of the freezer 120 though an access port 122 in the freezer cover 121 and retrieves one of the sample storage racks (not shown). To enable the retrieval module 110 to retrieve any sample storage racks in the freezer 120, the sample storage racks are stowed on a rack carrier (not shown in FIG. 1), which may be, for example, a rotatable drum, inside the freezer 120 and the motor assembly 130 controls the rotation of the rack carrier to position a given sample storage rack under the retrieval module 110.

Figure 2B:
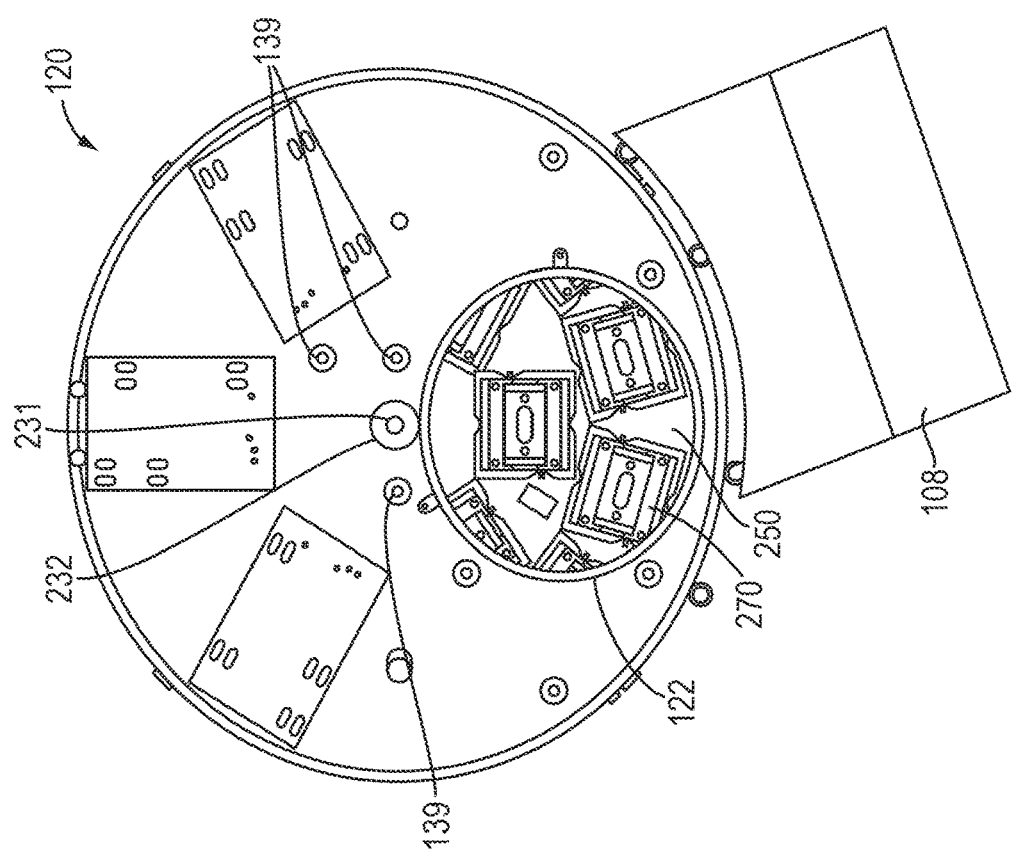
FIGS. 2A-B are illustrations of a cryogenic storage freezer in accordance with aspects of the disclosed embodiment.
Figure 2A:
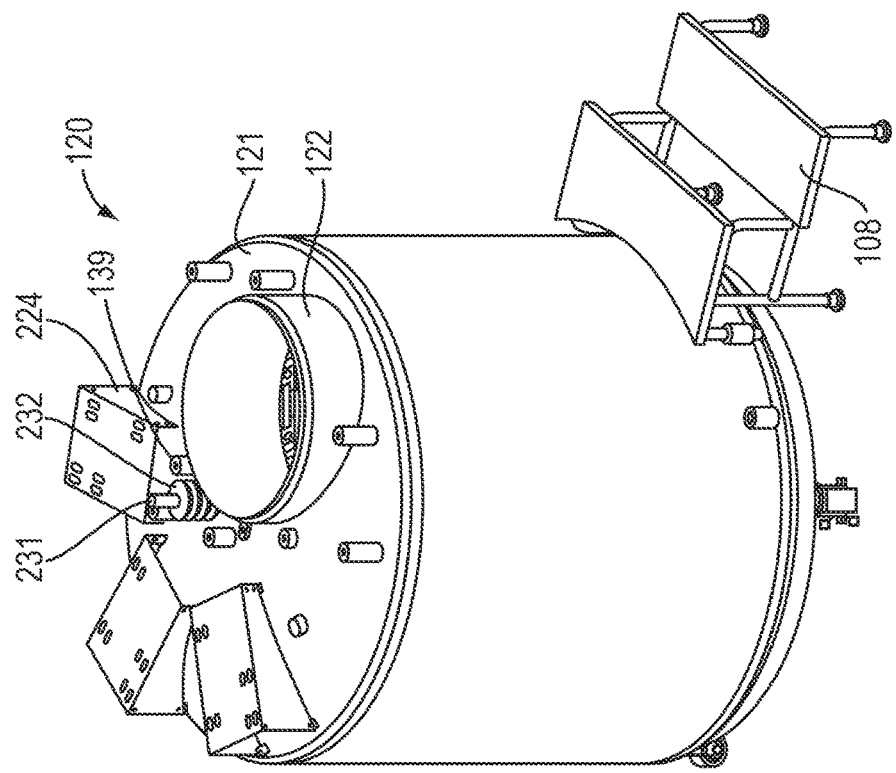

FIGS. 2A-B are illustrations of a cryogenic storage freezer in accordance with aspects of the disclosed embodiment. FIG. 2A shows the cryogenic storage freezer 120 configured for manual access. When configured for manual access, also referred to as in an automation-ready configuration, the freezer 120 lacks the retrieval module 110, motor assembly 130, and automated door 140 (as shown in FIG. 1). Instead, the freezer cover 121 includes mounting racks 224 configured to secure the retrieval module 110, and a drive shaft 231, covered by seal 232, protruding from the cover 121 with mounting studs positioned to secure a motor assembly to the freezer cover 121 for coupling with the drive shaft 231. The access port 122 of the freezer 120 is configured to accept a standard circular cryogenic freezer door (not shown). Seal 232 helps, for example, to prevent moisture from entering the freezer and to keep cold gas from escaping the freezer. In some embodiments, drive shaft 231 is constructed of a low thermally conductive material to minimize transmission of heat into the freezer.

FIG. 2B is a top-down view of the freezer 120 of FIG. 2A. FIG. 2B shows the top plate 250 of a rack carrier (shown in FIG. 3 as 360) positioned inside the freezer 120 through the access port 122 of the freezer cover 121. A rack carrier (shown as a rotatable drum) inside of the freezer 120 is configured to hold a plurality of sample storage racks and rotate inside of the freezer 120 to allow access to each sample storage rack though the access port 122. To hold the plurality of sample storage racks, a top plate 250 of the rack carrier holds a plurality of interface members 270, where each interface member 270 is attached to the top of a sample storage rack (not shown in FIG. 2B) and precisely positions the top of each sample storage rack in the rack carrier. The precise positioning of the interface members 270 in the top plate 250 of the rack carrier allows a retrieval module 110 to be attached to the freezer 120 and accurately access the position of each interface member 270 by rotating the top plate 250 via the drive shaft 231. In manual operation, a user standing on the stairs 108 may reach through the access port 122 and manually rotate the top plate 250 to present a desired interface member 270 to the user and allow the user to retrieve the sample storage rack attached to the interface member 270 by pulling the interface member 270 and sample storage rack through the access port 122.

Figure 3:
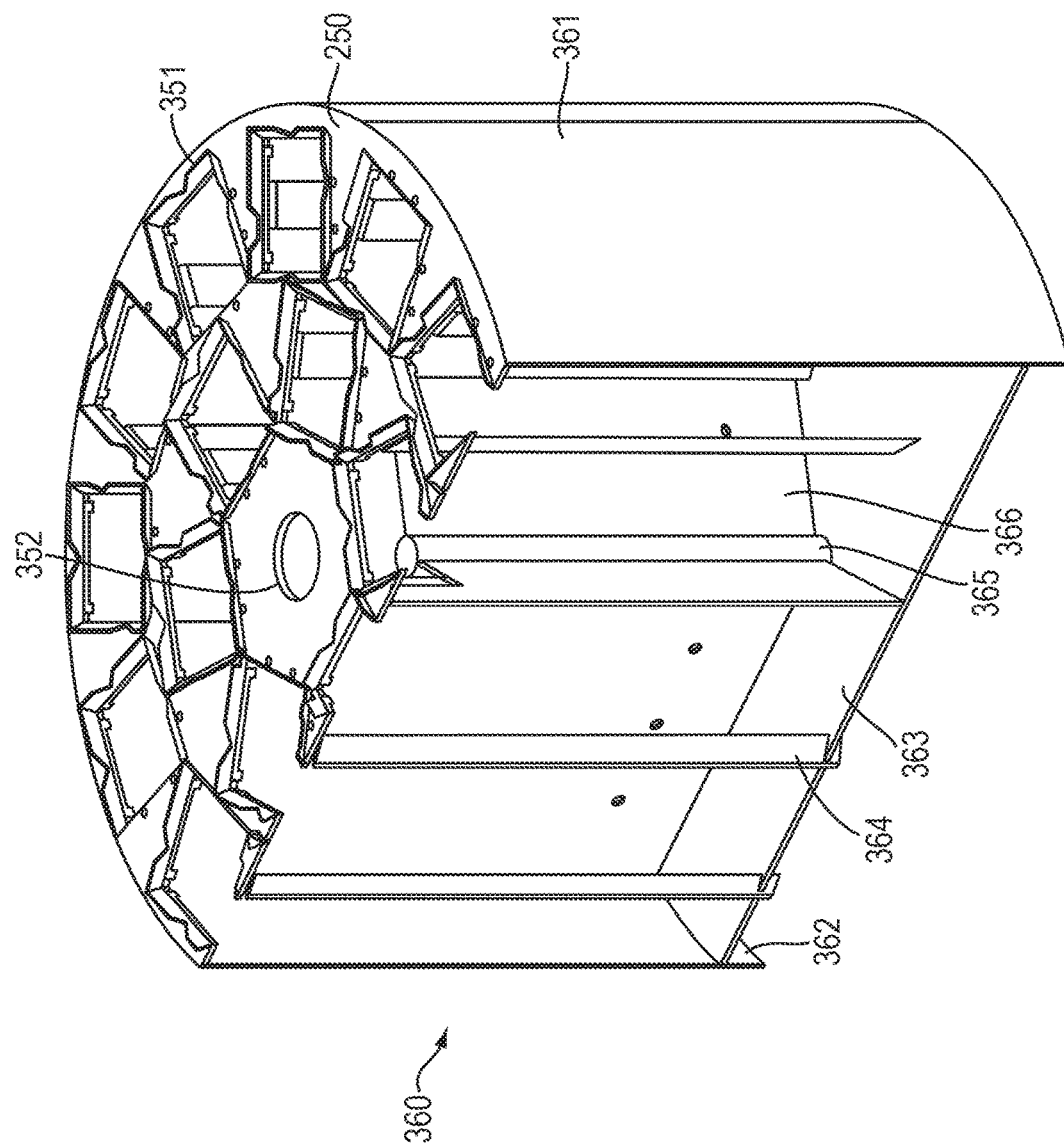
FIG. 3 is a cut-away illustration of a rack carrier and top plate in accordance with aspects of the disclosed embodiment.

FIG. 3 is a cut-away illustration of a rack carrier drum and top plate in accordance with aspects of the disclosed embodiment. FIG. 3 shows a rack carrier 360 with a top plate 250 having a plurality of rack-mounting features 351 positioned around the top plate 250. The rack carrier 360 comprises an outer wall 361 and a bottom plate 363. The outer wall 361 continues below the bottom plate 363 to a lower portion 362 configured to make contact with a pool of cryogenic fluid (not shown) resting at the bottom of the freezer 120. By contacting the cryogenic fluid, the lower portion 362 of the outer wall 361 conducts heat into the cryogenic fluid from the top plate 250 and plate 250 is a cooled thermal mass atop the rack carrier 360. The presence of the thermal mass improves the thermal storage efficiency of the rack carrier 360 by increasing heat absorption at the top of the rack carrier 360, which results in lower temperature gradients inside the rack carrier 360. Suitable configurations are shown, for example, in U.S. Pat. No. 6,393,847, entitled "Liquid Cryogen Freezer," the entire contents of which are hereby incorporated herein by reference. In preferred embodiments, the rack carrier is constructed of a material with high thermal conductivity (e.g., aluminum) to facilitate heat transfer and thermal uniformity within the freezer.

Also shown in FIG. 3, three stabilizing fins, also referred to as vertical support panels 366, radiate outward from a central shaft 365 of the rack carrier 360. The vertical support panels 366 may be affixed to the outer wall 361, lower panel 363, and the top plate 250, to increase the rigidity of the rack carrier 360. The top plate 250 may be connected to the outer wall 361 or the central shaft 365. A drive shaft opening 352 in the top plate 250 allows the drive shaft 231 to couple with the top plate 250 or the central shaft 365 of the rack carrier 360 and rotate the rack carrier 360 when the motor assembly 130 is connected to the drive shaft 231.

In operation, each rack-mounting feature 351 of the top plate 250 includes an opening sized to receive a sample storage rack (shown in FIG. 4 as 480) and support structures to position the sample storage rack in the opening and to enable each sample storage rack to hang from the top plate 250 without resting on the bottom plate 363 of the rack carrier 360, as shown in FIG. 5. Additionally, the rack carrier 360 includes support tabs 364 located adjacent to the vertical space below each rack-mounting feature 351 of the top plate 250. The support tabs 364 prevent sample trays stored in a sample storage rack adjacent the support tab from leaving the sample storage rack, and arrests the movement of the sample storage rack during rotation of the rack carrier 360.

Figure 4:
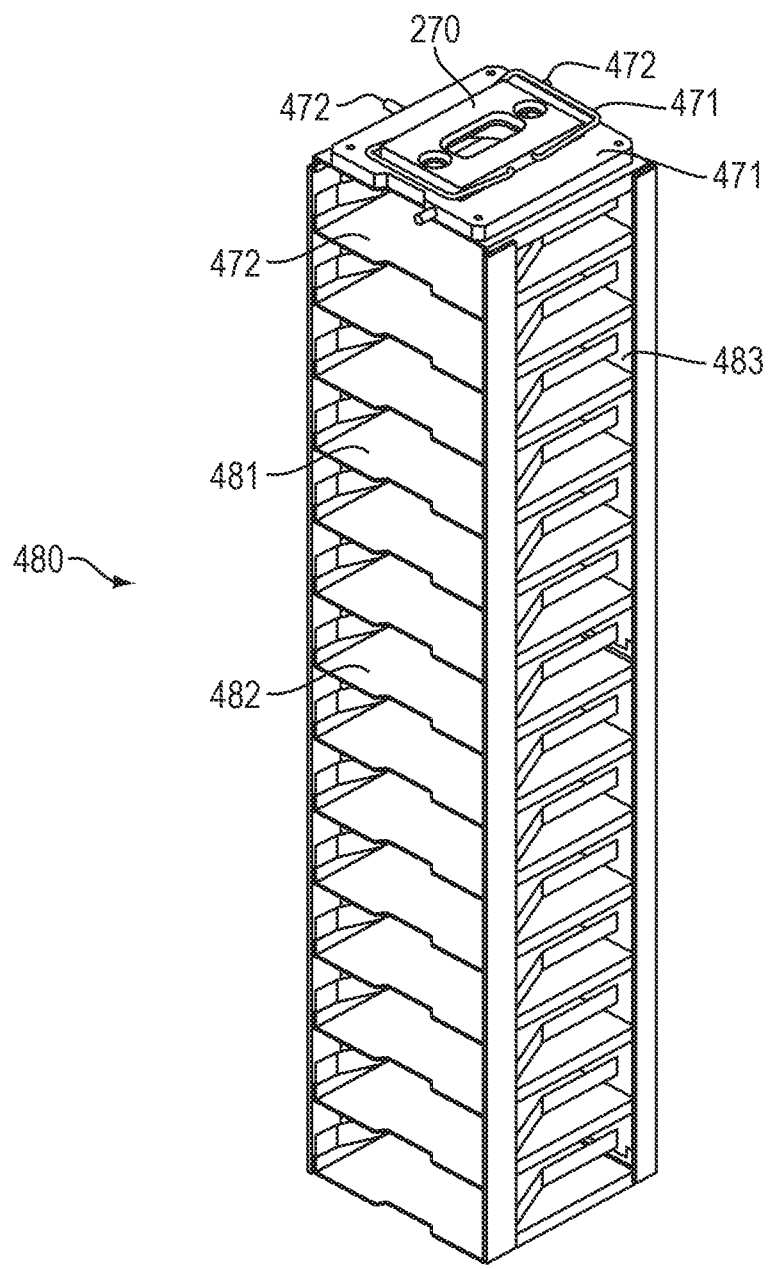
FIG. 4 is an illustration of storage rack with an attached interface member in accordance with aspects of the disclosed embodiment.

FIG. 4 is an illustration of storage rack with an attached interface member in accordance with aspects of the disclosed embodiment. FIG. 4 shows a sample storage rack 480 having an interface member 270 attached to the top of the sample storage rack 480. The sample storage rack 480 is configured to hold a plurality of sample storage trays (not shown), also referred to as storage boxes, by placing each sample storage tray on one of a plurality of vertically arranged shelves 481 spanning the length of the sample storage rack. Each shelf 481 has a pair of friction spring clips 483 configured to hold a sample storage stray (not shown) on the shelf 481. While sample storage rack 480 is illustrated as configured to hold rectangular sample storage trays (as shown, for example, in FIG. 20A-C), the sample storage racks can be configured to hold any shape sample storage trays. For example, in some embodiments, the sample storage trays and the sample storage rack have a triangular or pie-shaped horizontal cross section.

Also shown in FIG. 4, the interface member 270 attached to the top of the sample storage rack 480 includes a optional handle 471 enabling manual retrieval of the sample storage rack 480 when the sample storage rack 480 is hanging from the interface member 270, and the interface member 270 is resting on the top plate 250 of a rack carrier 360. The interface member 270 also includes three positioning pins 472 protruding outwardly from three corresponding sides of the interface member 270. The positioning pins 472 extend beyond the profile of the sample storage rack 480 and are positioned to interface with a rack-mounting feature 351 on the top plate 250.

FIGS. 5A-B are illustrations of a rack carrier with the top plate securing a plurality of sample storage racks by their respective interface members in accordance with aspects of the disclosed embodiment. FIG. 5A shows a perspective illustration of a rack carrier 360 with a portion of the outer wall 361 removed to show the arrangement of sample storage racks 480 secured to the top plate 250 of the rotatable storage drum 360 with interface members 270 attached to the top of the sample storage racks 480. Also shown are the support tabs 364 positioned against each sample storage rack 480.

FIG. 5B shows a lower-perspective illustration of a rack carrier 360 with a portion of the outer wall 361 removed to show the arrangement of sample storage racks 480 secured to the top plate 250 of the rotatable storage drum 360. The sample storage racks 480 hang from the top plate 250 and do not contact the bottom plate 363 of the rack carrier 360. In doing so, the position of sample storage racks 480 in the rack carrier 360 is determined by the top plate 250, as shown with more detail in FIG. 6.

FIG. 6 is an illustration of the top plate of and integrated rack-mounting features of FIG. 5A showing interface between the locating pins on the interface members and the rack-mounting features in accordance with aspects of the disclosed embodiment. FIG. 6 shows a top plate of a rack carrier 360 having a plurality of rack-mounting feature 351 each supporting an interface member 270. The rack-mounting features 351 include slanted guide fins 652 positioned to locate a sample storage rack 480 as it passes through the top plate 250. Each guide fin 652 includes a v-notch 653 or a flat-notch 654, where each notch 653, 654 is positioned to accept one of three positioning pins 472 on each interface member 270. Together, two v-notches 653 constrain the position of the interface member 270 in the plane of the top plate 250, and the v-notches 653 and flat-notch 654 together constrain the position of the interface member 270 in an axis orthogonal to the major plane of the top plate 250.

FIG. 7 is a cross-section illustration of a cryogenic storage freezer with a rack carrier coupled to a drive shaft and motor in accordance with aspects of the disclosed embodiment. FIG. 7 shows a freezer 120 in an automated-configuration with an attached motor assembly 130 and automated door 140. A rack carrier 360 is positioned inside an inner wall 725 of the freezer 120 and supported by a drive shaft 231 connected to the motor assembly 130. A refrigerant access port 109 supplies a cryogenic liquid to a bottom zone 729 of the freezer, the cryogenic fluid may pool and contact the lower portion 362 of the outer wall 361 of the rack carrier 360 to cool the top plate 250. The drive shaft 231 includes a spherical bearing 733 configured to rest against a race 729 coupled to the freezer cover 121. In a manual operation configuration, the rack carrier 360 hangs from the drive shaft 231 and is supported by the spherical bearing 733 seated against the race 729. In some embodiments, the drive shaft 231 may only be present once the freezer is configured for automatic rotation, e.g, the rack carrier 360 may be fully supported by a bearing in manual operation without the drive shaft 231. In the automated configuration shown in FIG. 7, the rack carrier 360 hangs from the drive shaft 231 and the drive shaft 231 may be supported from the motor assembly or an external drive system by, for example, a gear system.

When the freezer is constructed, a vacuum is drawn between the outer wall 123 and the inner wall 725 of the freezer 120, and the inner wall 725 may deform slightly as a result of stresses on the inner wall 725 from supporting the vacuum. A result of any deformation in the inner wall 725 is that the location of the race 729 is not precisely controlled and during manual operation, when the spherical bearing 733 of the drive shaft 231 is supporting the weight of the rack carrier 360 on the race 729, rotating the rack carrier 360 may cause precession of the long axis of the drive shaft 231. Precession of the drive shaft 231 is inconsequential during manual rotation, but could harm a motor assembly 130 attached to the drive shaft 231 by inducing stress on internal components of the motor assembly 130, and, as a result, on the motor mounts 139 during automated rotation of the rack carrier. Additionally, automated retrieval of a sample storage rack 480 requires an automated device to mate with an interface member 270 in a precise and predictable location in the freezer 120.

Continuing to refer to FIG. 7, to reduce stress on the motor assembly 130 and motor mounts 139, and to precisely locate the interface members 270 by leveling the top plate 250 in the freezer 120, the drive shaft 231 is held off the race 729 by the motor assembly 130. The motor mounts 139 enable the motor assembly 130 to be leveled, and, as a result, the rack carrier 360 and top plate 250 are leveled inside the freezer 120. To further increase the precision of the location of the top plate 250 with respect to rotations of the drive shaft 231 by the motor assembly 130, the rack carrier 360 may be connected to the drive shaft via the top plate 250, and the top plate 250 may be directly connected to the drive shaft 231 via a connection disc 734. Without directly connecting the top plate 250 to the drive shaft 231, torque applied to the rotatable freezer 360 may twist the rotatable freezer 360 and reduce the accuracy between the position of top plate 250 and the rotation of the drive shaft 231.

FIG. 8 is an isometric view of a cross-section of a cryogenic storage freezer with a rack carrier configured for manual operation in accordance with aspects of the disclosed embodiment. FIG. 8 shows a freezer configured for manual access and rotation of the rack carrier 360 though the access port 122 in the freezer cover 121. The drive shaft 231 is coupled to the top plate 250 of the rack carrier 360 via the connection disc 734 and the spherical bearing 733 of the drive shaft 231 rests on the race 729. In this manner, a user reaches into the freezer 120 and rotates the rack carrier 360 by gloved hand about the race 729. Once the user has presented a desired interface member 270 to the access port 122, the user retrieves the sample storage rack 480 from the freezer 120 by grasping the handle 471 of the interface member 270 and removes the sample storage rack 480 though the access port 122.

To configure the freezer 120 for automated rotation and retrieval of the sample storage racks 480, a motor assembly is attached to the motor mounts 239 and the drive shaft 231. To lift the spherical bearing 733 off of the race 729, the drive shaft may include a threaded exterior end (shown in FIG. 9 as 934). The threaded exterior end of the drive shaft 231 enables rotation of the rack carrier 360 to thread the drive shaft 231 into the motor assembly 130 and lift the spherical bearing 733 off the race 729. Once lifted, the drive shaft 231 may be locked into position in the motor assembly 130 to prevent further threading or de-threading of the drive shaft 231. The process of lifting and locking the drive shaft 231 is described in further detail below with reference to FIGS. 16 and 27A-B.

Figure 9:
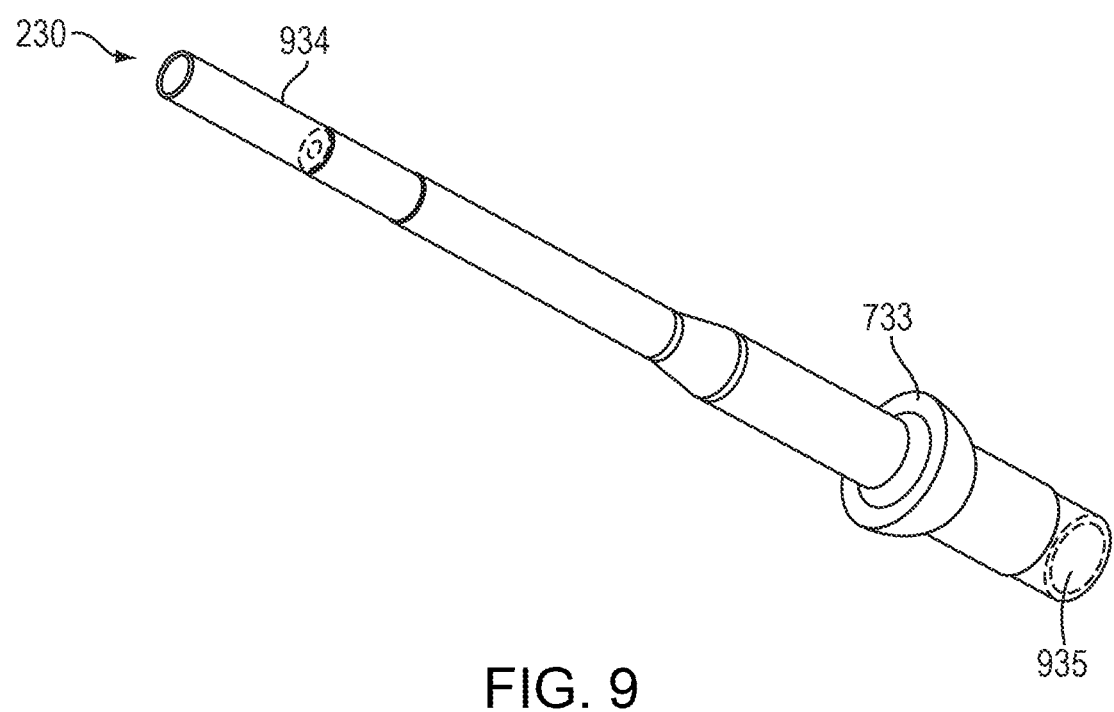
FIG. 9 is an illustration of the drive shaft of FIGS. 7 and 8 in accordance with aspects of the disclosed embodiment.

FIG. 9 is an illustration of the drive shaft of FIGS. 7 and 8 in accordance with aspects of the disclosed embodiment. FIG. 9 shows a drive shaft 230 including a threaded exterior end 934 adapted to be threaded into a motor assembly 130, an interior end 935 adapted to be coupled to a connection disc 734 or directly coupled to the top plate 250, and a spherical bearing 733.

Figure 10:
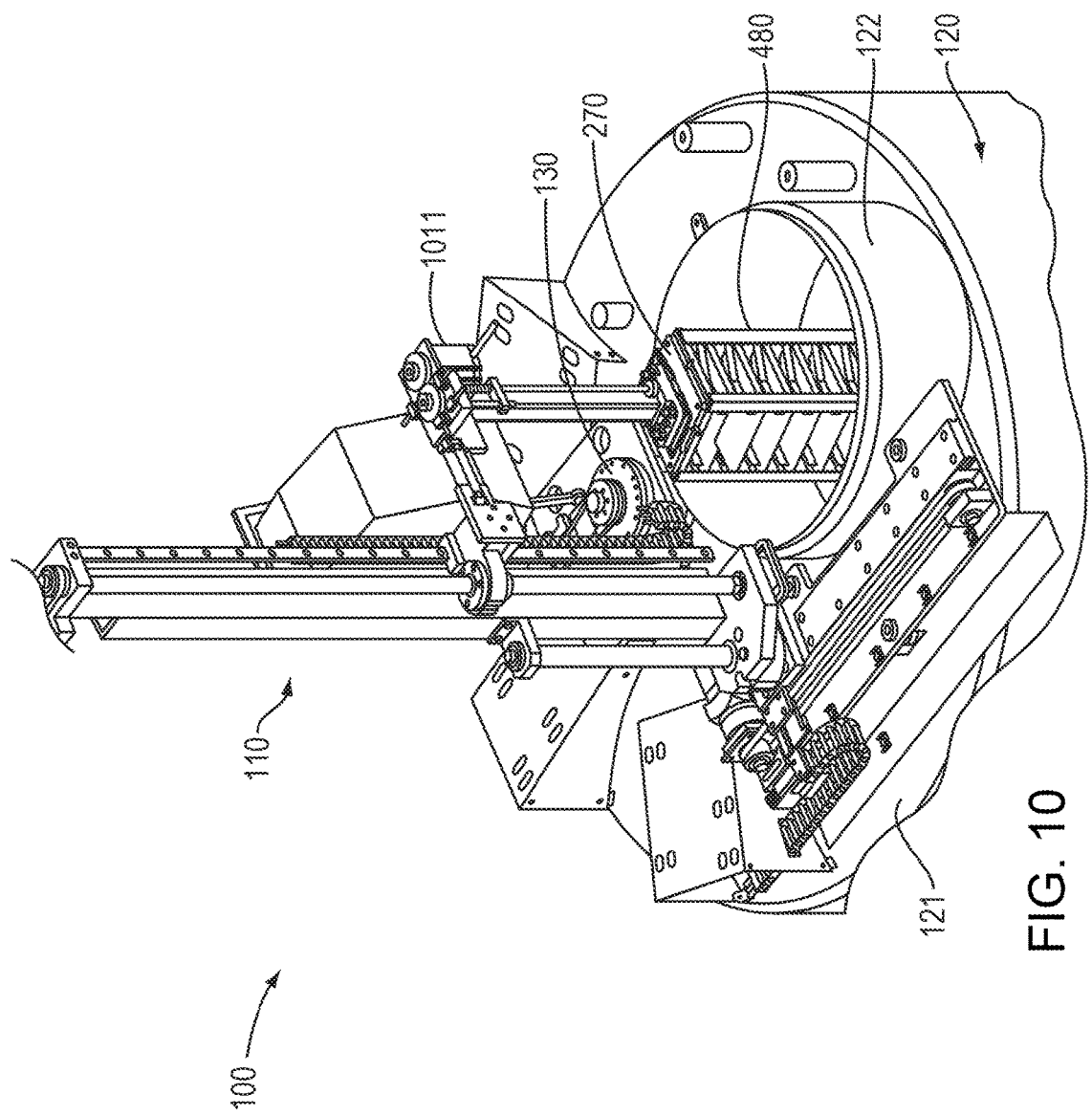
FIG. 10 is an illustration a retrieval module removed a sample storage rack from a freezer of in accordance with aspects of the disclosed embodiment.

FIG. 10 is an illustration of a retrieval module removing a sample storage rack from a freezer in accordance with aspects of the disclosed embodiment. FIG. 10 shows a configurable cryogenic storage device 100 including a retrieval module 11 and a freezer 120. To configure for automation, a retrieval module 110, including a gripping assembly 1011, is secured to the freezer cover 121 and the drive shaft lifts the rack carrier 360 and couples with a motor assembly 130 to enable automatic rotation of the rack carrier 360. In operation, the motor assembly 130 rotates the rack carrier 360 to a desired position and the gripping assembly 1011 is lowered into the freezer and mates with interface member 270 of a sample storage rack and to retrieves or stow the sample storage rack 480 though the access port 122 of the freezer 120.

FIGS. 11A-B are illustrations of a gripper assembly of a retrieval module mating with an interface member of a sample storage rack in accordance with aspects of the disclosed embodiment. FIG. 11A shows a gripping assembly 1011 having a gripping module 1112 positioned at a lower end and a sample storage rack 480 having an attached interface member 270. The gripping module 1112 is adapted to mate with the interface member 270 and secure the sample storage rack 480 to the gripping assembly 1011. The gripping module 1112 includes locating pins 1113, spring ejector pins 1114, and a sensing rod 1116. The interface member 270 includes a mounting surface 1173 supporting an attachment opening 1174, a circular locating hole 1175, and an oval locating hole 1176. The locating pins 1113 are provided to precisely locate the gripping module 1112 against the mounting surface 1173 prior to engagement of a T-latch (not shown) in the attachment opening 1174.

In operation, the gripping module 1112 is lowered against the interface member 270 and the locating pins 1113 enter the locating holes 1175, 1176 as the gripping module 1112 approaches the mounting surface 1173. The oval locating hole 1176 prevents thermal contraction or expansion of the interface member 270 from preventing the locating pins 1113 from entering both locating holes 1175, 1176. When mated with the locating pins 1113, the circular locating hole 1175 positions the gripping module 1112 about the plane of the gripping surface 1173, and the oval locating hole 1176 constrains the rotation of the gripping module 1112 about the centerline of the circular locating hole 1175. The spring ejector pins 1114 are compressed by the mounting surface 1173 when the gripping module 1112 is pressed against the mounting surface 1173. Compressing the spring ejector pins 1114 generates a force pushing the interface member 270 away from the gripping module 1112, and the force assists in subsequently decoupling the gripping module from the mounting surface 1173 by overcoming any adhesion that may result from, for example, ice or frost between the mounting surface 1173 and the gripping module 1112. As the gripping module 1112 is lowered, the sensing rod 1116 may, for example, deflect when contacting the mounting surface 1173 and use the deflection to sense the position of the mounting surface 1173 and indicate when a mating operation is able to begin, as shown in FIGS. 13A-C.

The sensing rod 1116 may also be used to detect frost build up on the mounting surface 1173, given a known position of the mounting surface 1173, by deflecting earlier than expected as a result of contact with frost on the mounting surface 1173 occurring prior to contact with the mounting surface 1173. Additionally, all three openings 1174-1176 in the mounting surface 1173 are through holes to prevent frost on the interface member 270 from being compacted into ice inside the openings when the gripping module 1112 mates with the interface member 270.

FIG. 11B shows the gripping module 1112 of the gripping assembly 1011 mated with the interface member 270. In the position shown, the spring ejector pins 1114 are compressed against the interface members 270 and the sensing rod 1116 is pushed upwards by the interface member 270. Additionally, the locating pins 1113 are positioned inside the locating holes 1175, 1176.

FIGS. 12A-B are cross-section illustrations of a gripping assembly mated to an interface member of a sample storage rack of in accordance with aspects of the disclosed embodiment. FIG. 12A shows the gripping module 1112 of the gripping assembly 1011 mated with the interface members 270 of a sample storage rack 480. FIG. 12B is a close-up view of Detail B of FIG. 12A. FIG. 12B shows the locating pins 1113 of the gripping module 1112 inside of the locating holes 1175, 1176 of the interface members 270. A T-latch 1218 is located under the mounting surface 1173 of the interface members 270. The T-latch 1218 is connected to a latch shaft 1217 inside the gripping assembly 1011. The T-latch 1218 is configured to pass through the attachment opening 1174 in the mounting surface 1173 and rotate under the mounting surface 1173 to secure the interface members 270 to the gripping module 1112, as shown in FIGS. 13A-C.

FIGS. 13A-C are illustrations of the latch of a gripping assembly mating with an interface member in accordance with aspects of the disclosed embodiment. FIG. 13A shows a T-latch 1218 of a gripping assembly 1011 prior to securing an interface member 270 to the gripping assembly 1011. FIG. 13B is a close-up view of Detail A of FIG. 13A. FIG. 13B shows an interface member 270 positioned against a gripping module 1112 of a gripping assembly 1011. The locating pins 1113 of the gripping module 1112 are inside the corresponding locating holes 1175, 1176 of the interface member 270 and the T-latch 1218 has passed through the adaptor opening 1174 in the mounting surface 1173. As shown in FIG. 13C, rotation of the T-latch 1218 by the latch shaft 1217 positions the ends of the T-latch 1218 under the mounting surface 1173 of the interface member 270 and enables the gripping assembly 1011 to lift a sample storage rack 480 coupled to the interface member 270.

Figure 14:
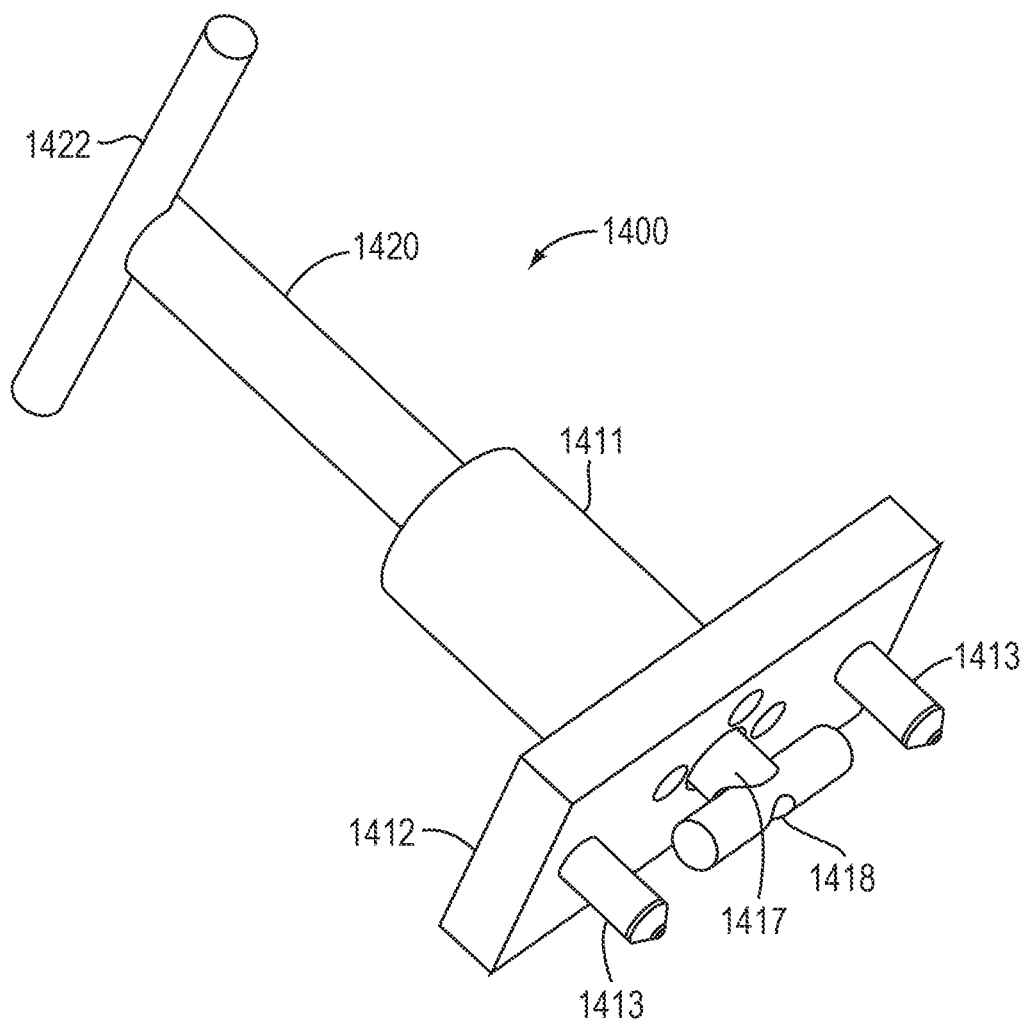
FIG. 14 illustrates a manual gripper device in one embodiment.

FIG. 14 is an illustration of a manual gripper 1400. The manual gripper 1400 may be configured to incorporate features comparable to those of the gripping assembly 1011 described above with reference to FIGS. 10-13C, but also includes features to enable manual manipulation of storage racks by a user. In particular, the manual gripper 1400 may include a plate configured to align with an interface member 270 of a storage rack, as well as locating pins 1413 provided to precisely locate the plate 1412 against the mounting surface 1173 prior to engagement of a T-latch 1418. The T-latch 1418 is connected to a lower shaft 1417, which engages with an upper shaft 1420 via an enclosure 1411. The upper shaft 1420, in turn, is connected to a T-bar 1422 for manual manipulation by a user.

The enclosure 1411 may house a spring or other device configured to maintain the lower shaft 1417 and T-latch 1418 in a retracted position toward the plate 1412. However, a user may apply a downward force on the T-bar 1422, causing the lower shaft 1417 and T-latch 1418 to extend to engage with an interface member 270 of a storage rack. By rotating the T-Bar 1422, the user can rotate the lower shaft 1417 and T-latch 1418 to lock with the interface member 270, thereby allowing the user to lift and carry the storage rack via the manual gripper 1400.

The interface member 270 of a storage rack, which accommodates the gripping assembly 1011 as described above with reference to FIGS. 13A-C, enables one to use the manual gripper 1400 to extract racks without grasping traditional rack handles using insulating gloves. The manual gripper 1400 thus enables easier manipulation of racks while wearing protective gear.

Turning again to FIG. 1, the automated cryogenic storage system 100, as described above, generally includes a cryogenic freezer 120 and an automation system 105 mounted to a top portion of the freezer 120. The freezer 120, as described above with reference to FIGS. 2-14, can be provided independently from the automation system 105, while including the features described above to enable operation with the automation system 105. Thus, the freezer 120 may be configured to operate in a "manual" mode absent from the automation system 105, as well as in an "automated" mode in combination with the automation system 105. Likewise, the automation system 105 may be provided independently from, or in conjunction with, the freezer 120. For example, the automation system 105 may be mounted to and configured to operate with the freezer 120 as a retrofit, converting the freezer 120 from a solely manually-accessible freezer to an automated freezer (i.e., the automated storage system 100). Example embodiments of an automation system 105 are described below.

Figure 15:
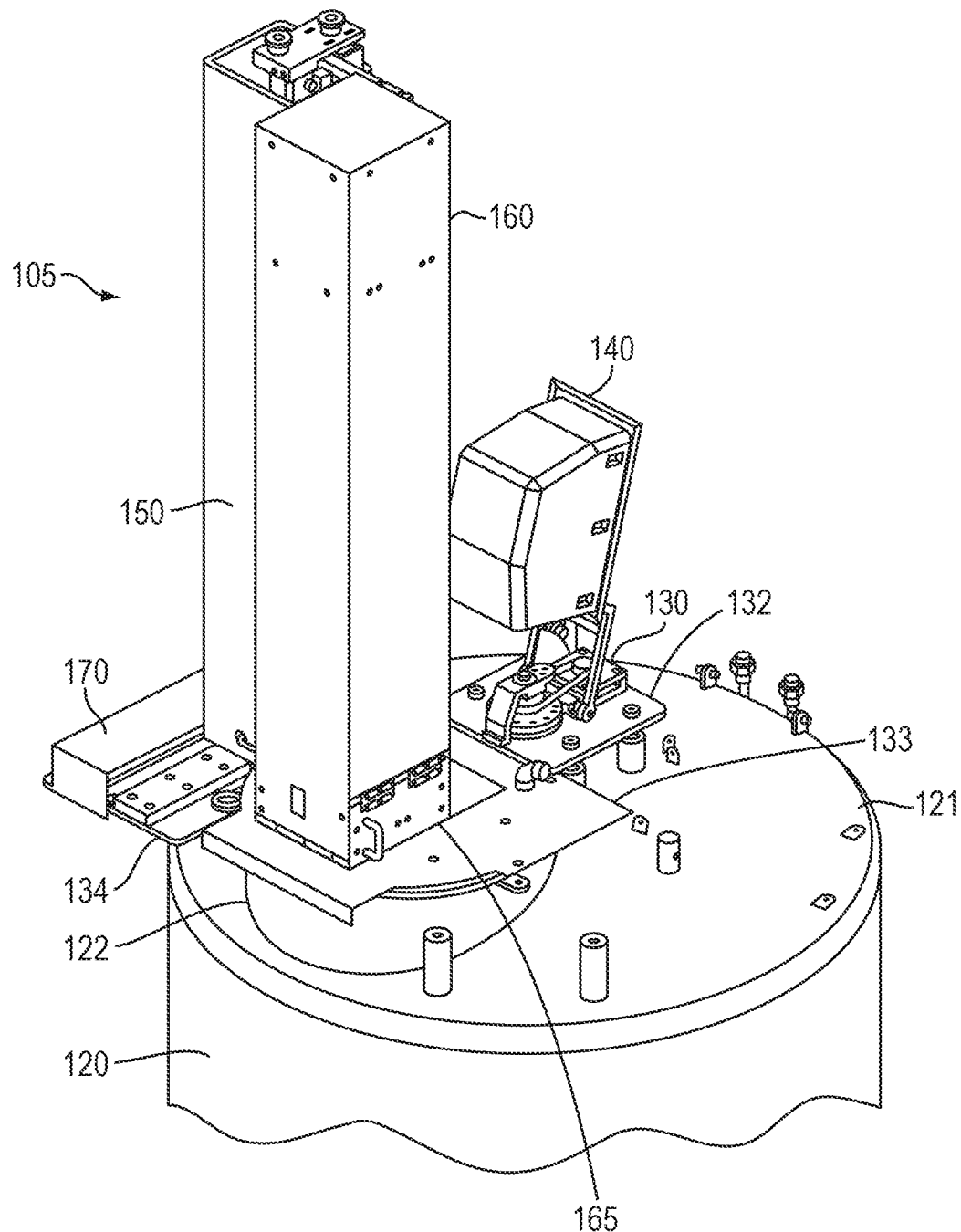
FIG. 15 illustrates an automated retrieval system in one embodiment.

FIG. 15 illustrates an automation system 105 for automated retrieval in one embodiment. The system 105 may be implemented in an automated cryogenic storage system such as the system 100 described above with reference to FIG. 1, and may incorporate features as described above. The automation system 105 operates to automatically retrieve and replace sample racks within the cryogenic freezer 120, which may be configured as described above with reference to FIGS. 1-14. The system 105 may be mounted to the freezer cover 121 via a number of mounts (e.g., mounts 132, 133, 134), and includes a motor assembly 130, an automated door 140, a rack puller 150, an insulating sleeve 160, and a conveyor 170.

The motor assembly 130 is mounted to the freezer cover 121 via a respective mount 132, and may operate to rotate a rack assembly within the freezer 120. For example, the motor assembly 130 may drive rotation of a rack carrier 360 as described above with reference to FIG. 3, for example to position a selected rack (e.g., rack 480 in FIG. 4) below the access port 122 of the freezer 120. The motor assembly 130 may also drive the removal and replacement of the automated door 140. As shown in FIG. 15, the door 140 is positioned in an upright or "open" position by the motor assembly 130, allowing access to the access port 122 of the freezer 120 during a sample transfer operation. When a sample rack is not being removed from or replaced to the freezer 120, the motor assembly 130 may lower the door 140 to a "closed" position where it forms a seal at the access port 122. Embodiments of the motor assembly 130 and automated door are described in further detail below with reference to FIGS. 16 and 17.

The rack puller 150 may include a gripper assembly 1011 as described above with reference to FIGS. 10-13B, and operates to latch onto a selected rack (e.g., rack 480 in FIG. 4) and elevate the rack through the access port 122 and into the insulating sleeve 160. The rack puller 150 may be supported by the conveyor 170, and may make sliding contact with the mount 133 at the access port 122. The insulating sleeve 160 may house a removed rack during a transfer operation, and includes insulated walls to maintain the removed rack below a threshold temperature during the operation. A sleeve port 165 enables a manual and/or automated transfer of sample boxes from and to the selected rack. Embodiments of the rack puller are described in further detail below with reference to FIGS. 18-19B, and embodiments of the insulating sleeve 160 are described in further detail below with reference to FIGS. 20A-D.

The conveyor 170 may include a motorized rail and carriage apparatus connected to the rack puller 150, and may operate to move and position the rack puller 150 and insulating sleeve 160 along a linear path relative to the access port 122 of the freezer 120. In particular, the conveyor 170 may position the rack puller 150 and insulating sleeve 160 away from the access port during opening and closing of the automated door 140. Further, during a rack transfer operation and following opening of the door 140, the conveyor 170 may move to position the rack puller 150 and insulating sleeve 150 above a selected rack, thereby enabling the rack puller 150 to elevate the selected rack through the access port 122 and into the insulating sleeve 160. In addition, the conveyor may enable manual and/or automatic rotation of the rack puller 150 and insulating sleeve 160 to enable a manual or emergency access to the freezer 120 or a particular rack. Embodiments of the conveyor 170 are described in further detail below with reference to FIGS. 21-23.

Figure 16:
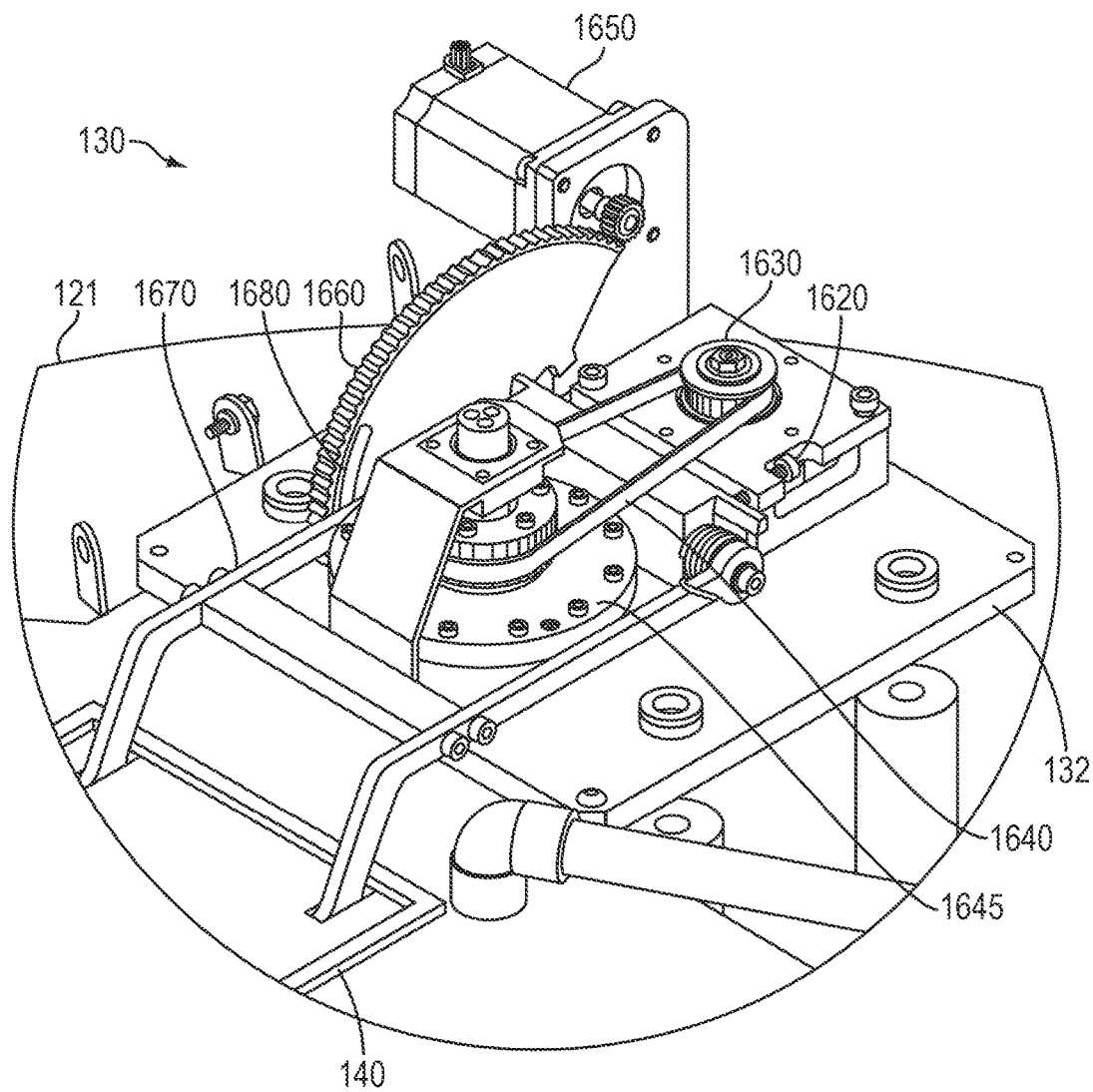
FIG. 16 illustrates an automated drive system in one embodiment.

FIG. 16 illustrates an automated motor assembly 130 (also referred to as a "drive system") in one embodiment. The motor assembly 130 may be configured as described above with reference to FIGS. 1 and 15. In particular, the motor assembly 130 may be mounted to a freezer cover 121 via a mount 132, and may operate to rotate a rack carrier within the freezer 120. To provide such operation, a motor 1620 (shown in further detail in FIG. 17) operates a gear assembly 1630 to control rotation of a central gear 1640, which is, in turn, coupled a drive shaft (e.g., drive shaft 230 in FIG. 7) to rotate the rack carrier (e.g, rack carrier 360 in FIG. 3). Alternatively, the motor 1620 may be directly connected to the drive shaft rotating the rack carrier. A locking plate 1645, located below the central gear 1640, is configured to engage with the drive shaft 231 to lift and lock the drive shaft 231 into position. The locking plate is described in further detail below with reference to FIGS. 27A-B.

The motor assembly 130 may also drive the removal and replacement of the automated door 140. An additional motor 1650 drives a gear 1660, which in turn connects to a door bracket 1670 supporting the door 140. The door bracket 1670 may extend into a slot 1680 located toward one end of the gear 1660. The slot 1680 enables a range of movement for the bracket 1670 within the gear 1660, and thus prevents the motor assembly 130 from forcing the door 140 to be sealed via the gear 1660. Rather, the door 140, once lowered by the motor 1650, may remain closed due to the weight of the door 140, and can be lifted manually to a given extent by a user. This feature may enable the door 140 to be lifted manually, regardless of the status of the motor assembly 130, to access to samples. For example, sample racks may be accessed during an emergency condition such as a power outage affecting the motor assembly 130.

As shown in FIG. 16, the door 140 is positioned in an upright or "open" position by the motor assembly 130, allowing access to the access port 122 of the freezer 120 during a transfer operation. When a sample rack is not being removed from or replaced to the freezer 120, the motor assembly 130 may lower the door 140 to a "closed" position where it forms a seal at the access port 122.

Figure 17:
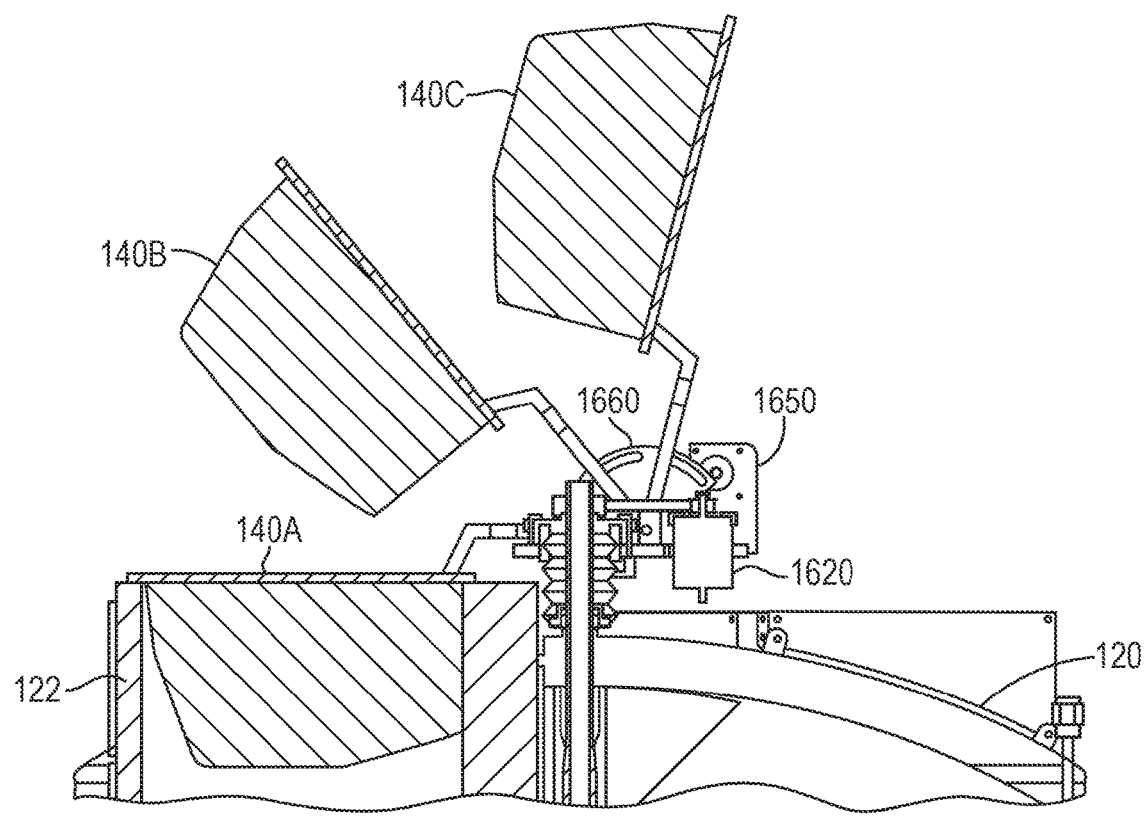
FIG. 17 illustrates a freezer door operable with the drive system of FIG. 16.

FIG. 17 illustrates a cross-sectional view of the motor assembly 130 and the door 140 described above with reference to FIG. 16. The door 140 may be comprised of a metal (e.g., stainless steel) upper surface, as well as a foam underportion that is shaped to insert into the freezer access port 122 to form substantially a thermal seal between the freezer 120 interior and the external (e.g., uncontrolled) environment. Here, the door 140 is shown in three positions along its range of movement as controlled by the motor 1650 and gear 1660: a "closed" position forming a seal with the access port 122 (140A); a partially open position (140B); and a fully open position where the door 140 is entirely cleared from the vertical space above the port 122 (140C). When in the fully open position (140C), the door enables removal and replacement of racks (e.g., rack 480 in FIG. 400) within the freezer 120, as well as the positioning of a rack puller and insulating sleeve above the access port 122 as shown, for example, in FIG. 15. In further embodiments, the foam underportion may be reduced in size or eliminated altogether and replaced with an alternative underportion, such as a layer of neoprene or other insulating material. By reducing the size and surface area of the underportion of the door 140, frost buildup on the underside of the door 140 may be reduced.

Figure 18:
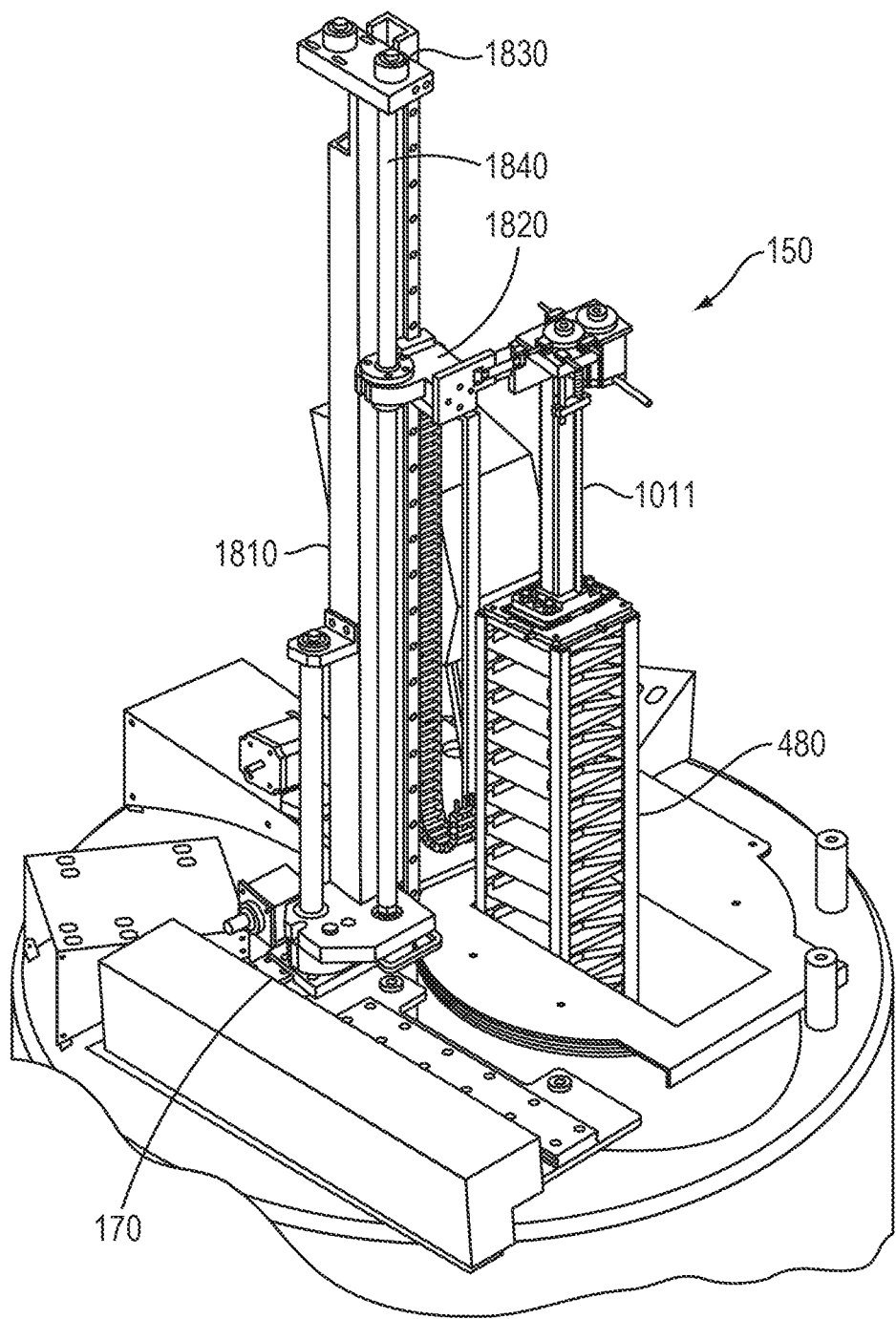
FIG. 18 illustrates rack puller assembly in one embodiment.

FIG. 18 illustrates rack puller 150 in one embodiment. In contrast to the embodiment shown in FIG. 16, the rack puller 150 is shown absent an outer cover and an associated insulating sleeve (e.g., 160 in FIG. 16) to illustrate its internal components, including a pillar 1810, a threaded shaft 1840, a shaft motor assembly 1830, a bracket 1820, and a gripper assembly 1011. The pillar 1810 generally supports the remaining components, and may be mounted to the conveyor 170 as described below with reference to FIGS. 21-23. The shaft motor assembly 1830 operates to rotate the threaded shaft 1840, which in turn causes the bracket 1820 and gripper assembly 1011 to move vertically along the length of the threaded shaft 1840. The threaded shaft 1840 may include a coarse threading and/or other features to enable the bracket 1820 and gripper assembly 1011 to be moved manually along the threaded shaft 1840, such as in the event of a power outage to the rack puller 150. The gripper assembly 1011 may be configured as described above with reference to FIGS. 10-13C, and, in particular, may operate to engage with a sample rack 480 to enable the rack puller 150 to elevate and lower the sample rack 480.

Figure 19A:
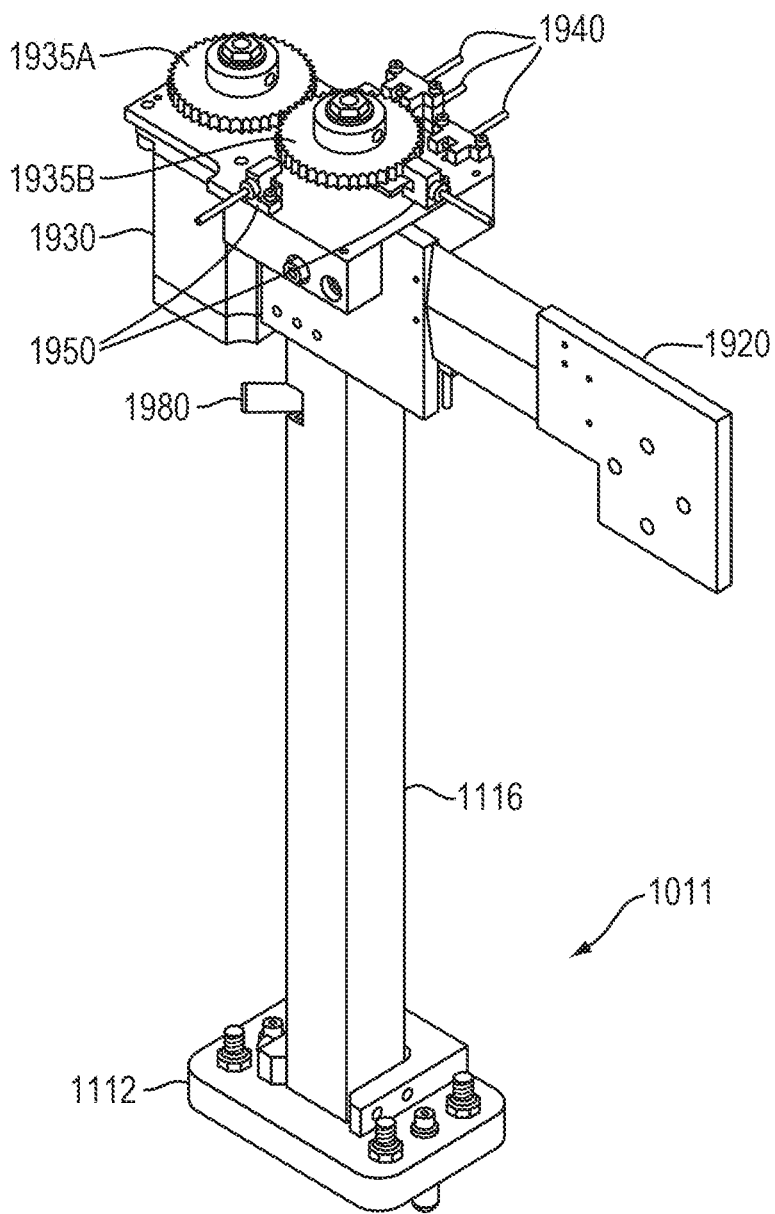
FIGS. 19A-B illustrate a gripper assembly in one embodiment.
Figure 19B:
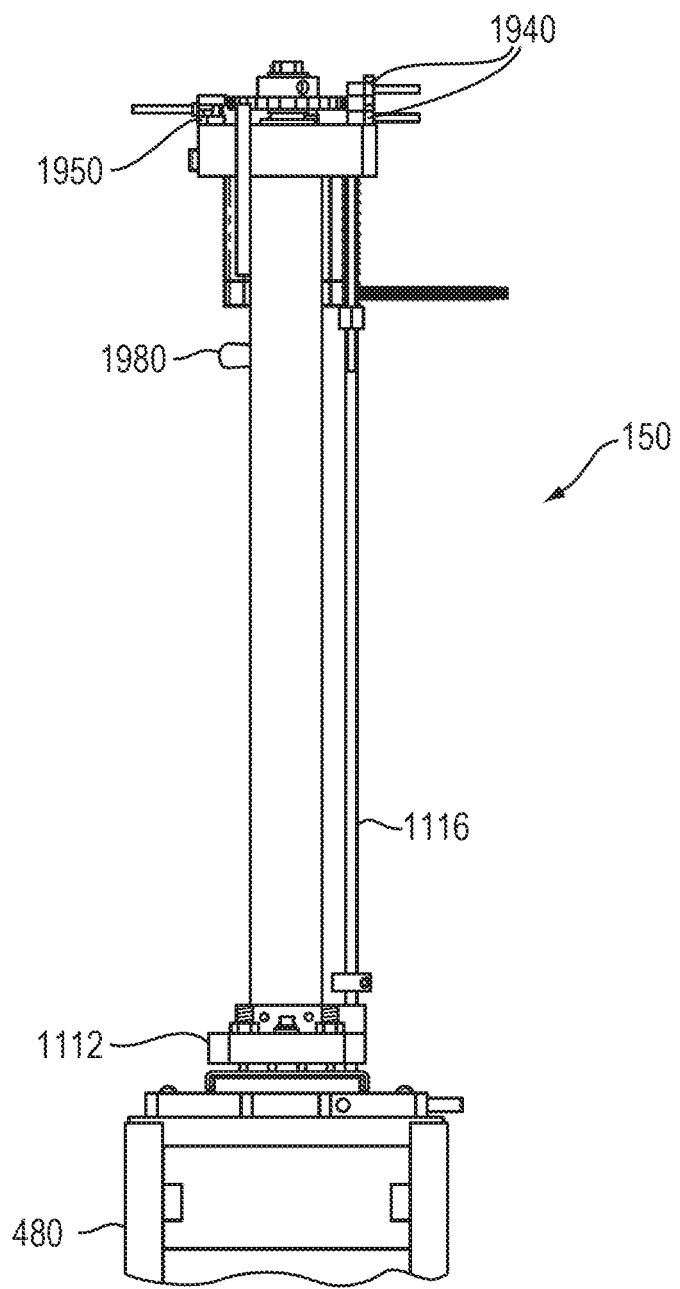

FIGS. 19A-B illustrate a gripper assembly 1011 in one embodiment. Features of the gripper assembly 1011 relating to the gripper interface 1112 are described above with reference to FIGS. 10-13C. In addition to the aforementioned features, the gripper assembly 1011 may include a bracket interface 1920 for coupling to a bracket 1820 as shown in FIG. 18, as well as features supporting an automated latching operation. As shown in FIG. 19A, in particular, the gripper assembly may include a motor 1930 configured to rotate a gears 1935A-B. The gear 1935B may be further connected to an internal shaft (shown in FIG. 12B as shaft 1217) extending through the length of the gripper assembly 1011, thereby rotating a locking mechanism (e.g., T-latch 1218 in FIG. 12B) to engage and disengage with an interface of a sample rack. In order to provide feedback to control such operations, the gripper assembly 1011 may also include one or more sensors 1940, 1950. Rotation sensors 1950 can detect a threshold rotation of a gear of the gear 1935B to determine the rotational position of the locking mechanism, which may indicate a locked or unlocked state. The rotation sensors 1950 may include optical or infrared beam sensors that provide an indication when a corresponding beam is obstructed.

Depth sensors 1940 indicate one or more threshold distances between the gripper interface 1112 and a sample rack 480 with which it is to engage. As shown in FIG. 19B, the sensors 1940 may be located above a sensing rod (described above with reference to FIGS. 11A-B) and provide an indication when detecting the sensing rod 1116. For example, the depth sensors may include optical or infrared beam sensors that indicate when a corresponding beam is obstructed by the sensing rod 1116. By detecting the presence of the sensing rod 1116 and/or another rod in one or more locations during a latching operation, the depth sensors 1940 may indicate the one or more of the following: 1) a first threshold distance between the gripper interface 1112 and the rack 480, indicating the presence of the rack 480; 2) a second threshold distance indicating an appropriate distance in which to engage a locking mechanism at the gripper interface 1112; and 3) a third threshold distance indicating that a portion of the gripper interface 1112 (e.g., a locking mechanism) has extended an unacceptable distance. Due to the varying conditions such as differing rack placement and buildup of frost at the top surface of the rack 480 and/or the bottom surface of the gripper interface 1112, the gripper assembly 1011 may be met with a number of physical variations during successive rack retrieval operations. Accordingly, the sensors 1940, 1950 may assist to precisely engage with a series of racks despite such varying conditions.

Figure 20A:
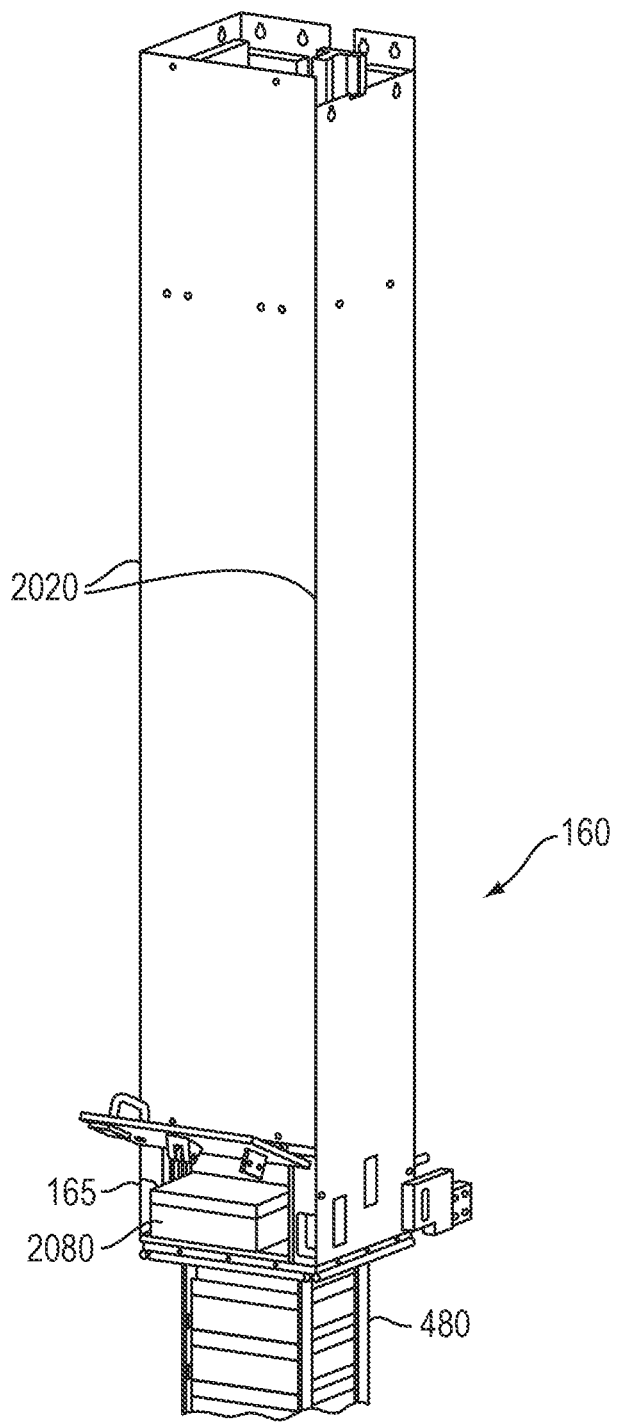

FIGS. 20A-D illustrate an insulating sleeve 160 in one embodiment. The insulating sleeve may be configured as described above with reference to FIGS. 1 and 15. In particular, the insulating sleeve may be mounted to a freezer cover 121 via a rack puller 150 and conveyor 170. As shown in FIG. 20A, the insulating sleeve 160 may house a rack 480 removed from a freezer during a rack retrieval operation, and includes insulated walls 2020 to maintain the removed rack 480 below a threshold temperature during the operation. The walls 2020 of the insulated sleeve 160 may extend to a height to accommodate both the full length of a rack 480 when fully removed from the freezer, as well as the length of a gripper assembly (e.g., gripper assembly 1011 in FIGS. 18-19) used to elevate the rack 480. A sleeve port 165 having a door 2075 enables access to a given shelf of the rack 480, where the insulating sleeve 160 may provide for manual and/or automated transfer of a sample box 2080 from and to the rack 480.

FIGS. 20B-C show a side cross-sectional view of a lower portion of the insulating sleeve 160 during transfer of a sample box 2080. As shown in FIG. 20B, the sample box 2080 is housed within the insulating sleeve 160 (and on a shelf of the rack) before or after a transfer. The sleeve port 165 is covered, in a sealed or unsealed manner, by the sleeve door 2075, which may include a handle 2070 for manual removal. A motor 2030, located at a rear side of the sleeve 160 opposite the door 2075, may operate to drive an ejection rod 2035 toward the sample box 2080, pushing the box 2080 at least partially through the port 165 as shown in FIG. 20C. A sensor 2095 may indicate the presence or position of the box 2080. During an automated ejection of the box 2080, if the sensor detects that the box 2080 has reached a threshold distance outside of the port 165, the sensor 2095 may provide a signal to the motor 2030 to cease driving the ejection rod 2035. At this point, a user may manually remove the box 2080 from the sleeve port 165 entirely.

During replacement of the sample box 2080 into a shelf of a rack, a user may insert the box 2080 into the sleeve port 165 as shown in FIG. 20C. Upon closing the door 2075 of the port 165, a door bumper 2055 may push the box 2080 further to ensure that the box 2080 is located entirely within the shelf of the rack. A sensor such as the sensor 2095 may also indicate the presence and/or location of the box 2080 to further ensure that the box 2080 is properly positioned. Once the box 2080 is verified to be positioned within the rack, the rack may be lowered or elevated within the sleeve, for example to remove or replace another sample box, or to replace the rack into the freezer.

Figure 20D:
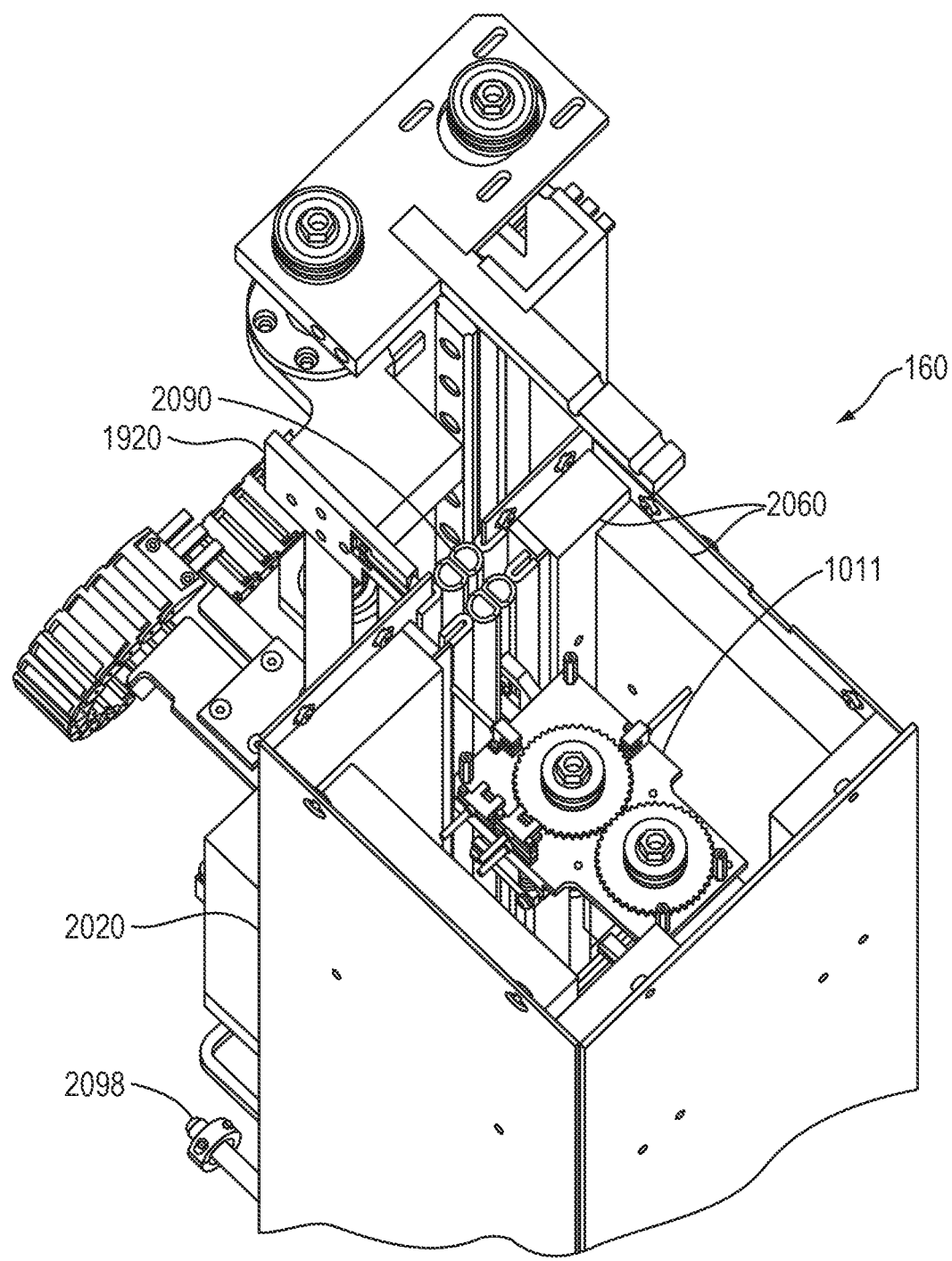

FIG. 20D illustrates a top portion of the insulating sleeve 160. Here, it is shown that each of the walls 2020 of the sleeve 160 include a respective insulating layer 2060 (comprising, for example, a foam or other insulating material). One of the walls 2020 further includes a 2-layer gasket 2090 extending the length of the wall. The gasket 2090 accommodates a bracket 1920 supporting a gripper assembly 1011 from the rack puller 150 as described above, enabling the gripper assembly 1011 to be elevated and lowered through the length of the insulating sleeve 160, while minimizing transfer of air between the inside of the sleeve 160 and the surrounding environment, which may be uncontrolled. Although the insulating sleeve 160 may or may not form an airtight seal between the inside of the sleeve 160 and the surrounding environment, minimizing such air transfer may assist in minimizing thermal and moisture transfer to a sample rack within the sleeve 160. Other features to support minimizing air transfer can include forming the insulating layers 2060 to closely accommodate the rack with minimal space between the rack and the layers 2060, as well as a cover (not shown) enclosing the top of the sleeve 160.

Further, the insulating sleeve 160 may accommodate a gas inlet 2098 to channel an expellant gas (e.g., nitrogen gas) into the sleeve 160. Although the sleeve 160 may generally encompass an uncontrolled environment, during a transfer operation, an expellant gas may be channeled into the sleeve 160 to minimize moisture and/or the temperature within the sleeve 160. The expellant gas may be channeled shortly before, or concurrently when, a rack is elevated into the sleeve 160. Following removal of the rack from the sleeve 160, the inside of the sleeve 160 may be allowed to return to an uncontrolled environment, at which it may remain until a concurrent transfer operation.

FIGS. 21A-C illustrate a top-down view of a conveyor 170 and operation with respect to an automation system and freezer 120 in one embodiment. The conveyor 170 may be configured as described above with reference to FIG. 15. In particular, the conveyor may be mounted to a freezer cover 121 via a respective mount 134. The conveyor 170 may include a motorized rail and carriage apparatus (shown in further detail in FIG. 22, described below) and is connected to the rack puller 150, supporting both the rack puller and the insulating sleeve 160. The conveyor 170 may operate to move and position the rack puller 150 and insulating sleeve 160 along a linear path relative to the access port 122 of the freezer 120. Three different positions attainable by the conveyor 170 are shown, respectively, in FIGS. 21A-C.

In FIG. 21A, the conveyor 170 positions the insulating sleeve 160 above a rack located beneath the access port 122 at an inner circle of the rack carrier. In contrast, in FIG. 21B, the selected rack is located at an outer circle of the rack carrier. Accordingly, the conveyor 170 positions the insulating sleeve 160 above the access port 122 and above the rack at an outer circle of the rack carrier. In both of the positions shown in FIGS. 21A and 21B, the rack puller 150 and insulated sleeve 160 are positioned to engage with a selected rack and elevate the selected rack from the freezer 120 into the insulating sleeve 160. During opening and closing of the automated door 140, the rack puller 150 and insulating sleeve 160 must be entirely clear of the access port 122. Thus, as shown in FIG. 21C, the conveyor 170 may also position the insulating sleeve 160 and rack puller 150 away from the access port 122, allowing the automated door 140 to be removed from or replaced to the access port 122.

Figure 22:
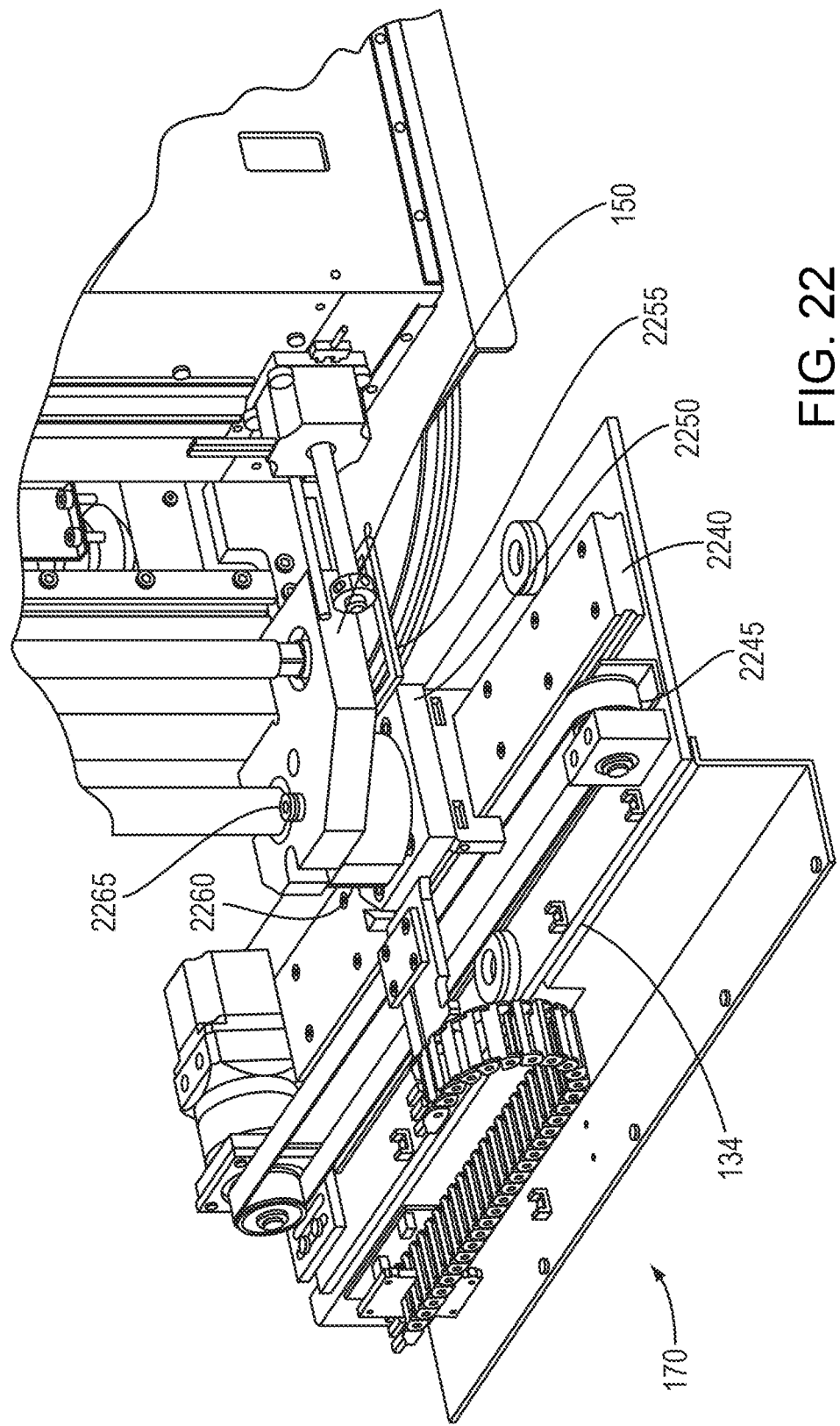
FIG. 22 illustrates a junction portion of a conveyor and rack puller assembly.

FIG. 22 illustrates a junction portion of a conveyor 170 and rack puller 150. The conveyor 170 includes a motorized belt drive 2245 and a rail 2240 mounted to a respective mount 134, as well as a carriage plate 2250 configured to move along the rail 2240 under control of the belt drive 2245. The carriage plate 2250 further supports a pivot shaft 2260 to connect to a complementary portion of the rack puller 150. The pivot shaft 2260 may form a rotatable connection with the rack puller 150 that is fixed by a manual release, such as a release pin 2265 or, alternatively, a switch. With the release pin 2265 engaged, the pivot shaft 2260 maintains a stationary connection with the rack puller 150. With the release pin 2265 disengaged (i.e., removed), the pivot shaft 2260 enables the rack puller 150 to rotate horizontally, allowing manual or emergency access to the freezer access port 122 or a rack located within the insulating sleeve. Further, a manual brake release arm 2255 controls a lock restricting manual vertical movement of the rack puller 150. When the brake release arm 2255 is disengaged, the rack puller 150 may be manually controlled to raise or lower a rack engaged by the rack puller 150. Thus, both the release pin 2265 and the brake release arm 2255 enable a rack to be manually accessed and moved as needed, such as in the event of an emergency or a power outage.

Figure 23B:
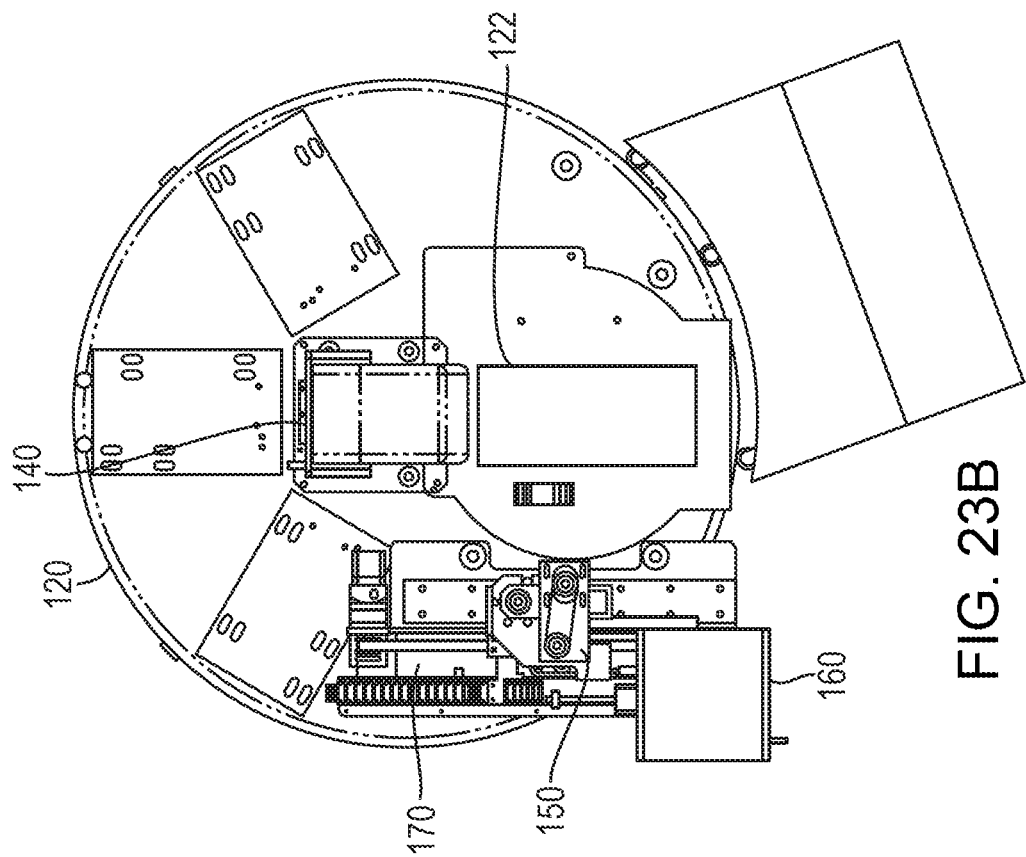
FIGS. 23A-B illustrate rotation of the rack puller assembly for manual access.
Figure 23A:
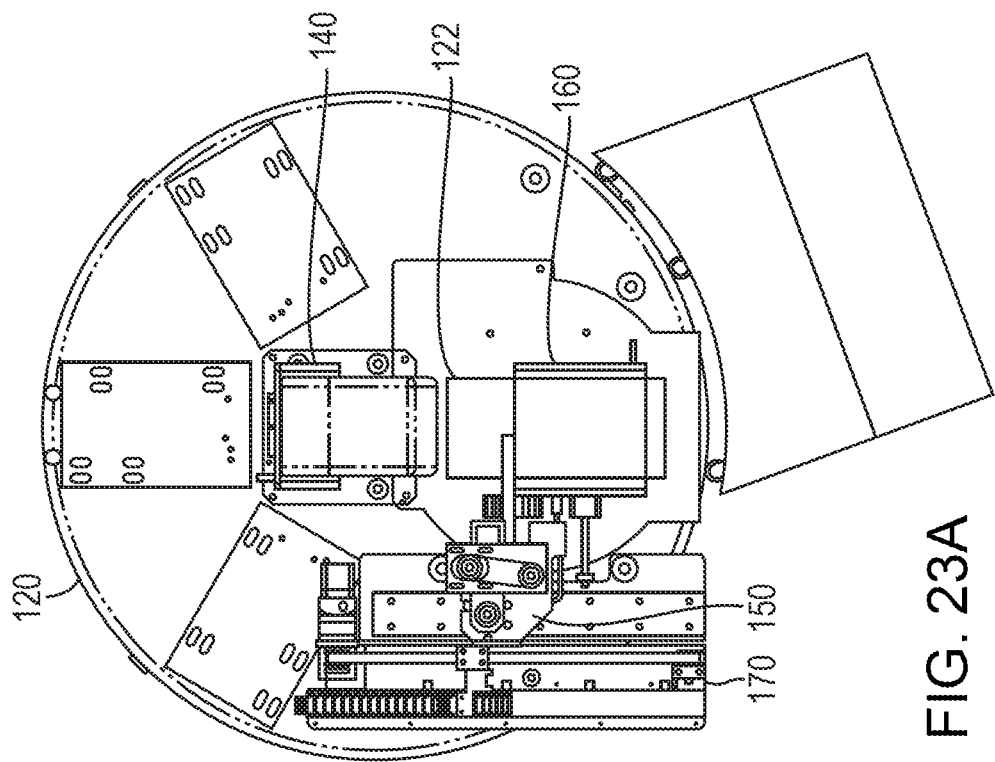

FIGS. 23A-B illustrate rotation of the rack puller 150 and insulating sleeve 160 as a result of disengaging the release pin 2265 as described above with reference to FIG. 22. In FIG. 23A, the rack puller 150 and insulating sleeve 160 are shown during a rack transfer operation. Following disengagement of the release pin 2265 of the conveyor 170, the rack puller 150 and insulating sleeve 160 can be rotated clockwise as shown in FIG. 23B. As a result, of this rotation, the access port 122 of the freezer 120 may be accessed manually. In addition, if a sample rack is located within the insulating sleeve 160, the sample rack may be manually removed from the insulating sleeve 160 away from the freezer 120.

Figure 24:
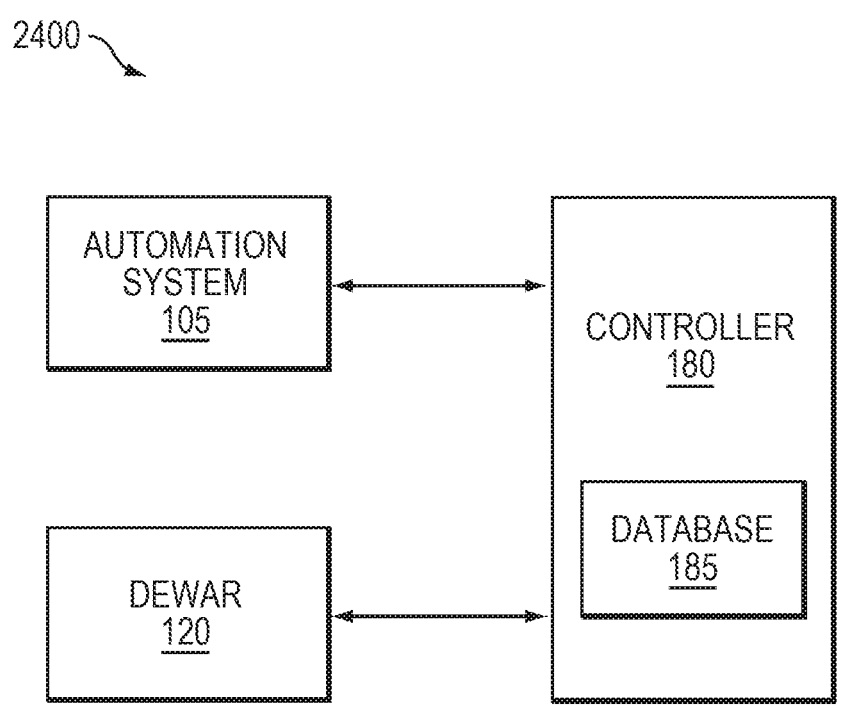
FIG. 24 is a block diagram of an automated cryogenic storage system including a controller in one embodiment.

FIG. 24 is a block diagram of an automated cryogenic storage system 2400 including a controller 180 in a further embodiment. The system 2400 may include the features of the cryogenic storage system 100 described above with reference to FIGS. 1-23, including the sample automation system 105 and freezer 120, and further includes a controller 180. The controller 180 may be connectively coupled to the automation system 105 and freezer 120, and generally controls some or all of the operations of each. For example, the controller 180 may monitor and regulate temperature, humidity, and other conditions within the freezer 120. The controller 180 may also control the automation system 105 (e.g., motor assembly 160, rack puller 150, insulating sleeve 160, and conveyor 170) to manage and control the transfer of samples to and from the freezer 120. The controller 180 may also control other operations such as calibration of mechanical components, identifying samples, and failure or disaster recovery. Further, the controller may maintain a database 185 storing information regarding the samples stored within the freezer 120, including the location of each sample (i.e., rack and sample box) within the freezer 120.

The controller 180 may update the database 185 in response to the transfer of samples into or out of the freezer 120.

To provide such control operations, the controller 180 may include suitable computer hardware and software resources, such as one or more computer workstations and an interface configured for communication with the automation system 105 and freezer 120. The controller 180 may also include an interface (e.g., a workstation) allowing a user to monitor the system 2400 as well as monitor an initiate the aforementioned operations of the system 2400.

Figure 25:
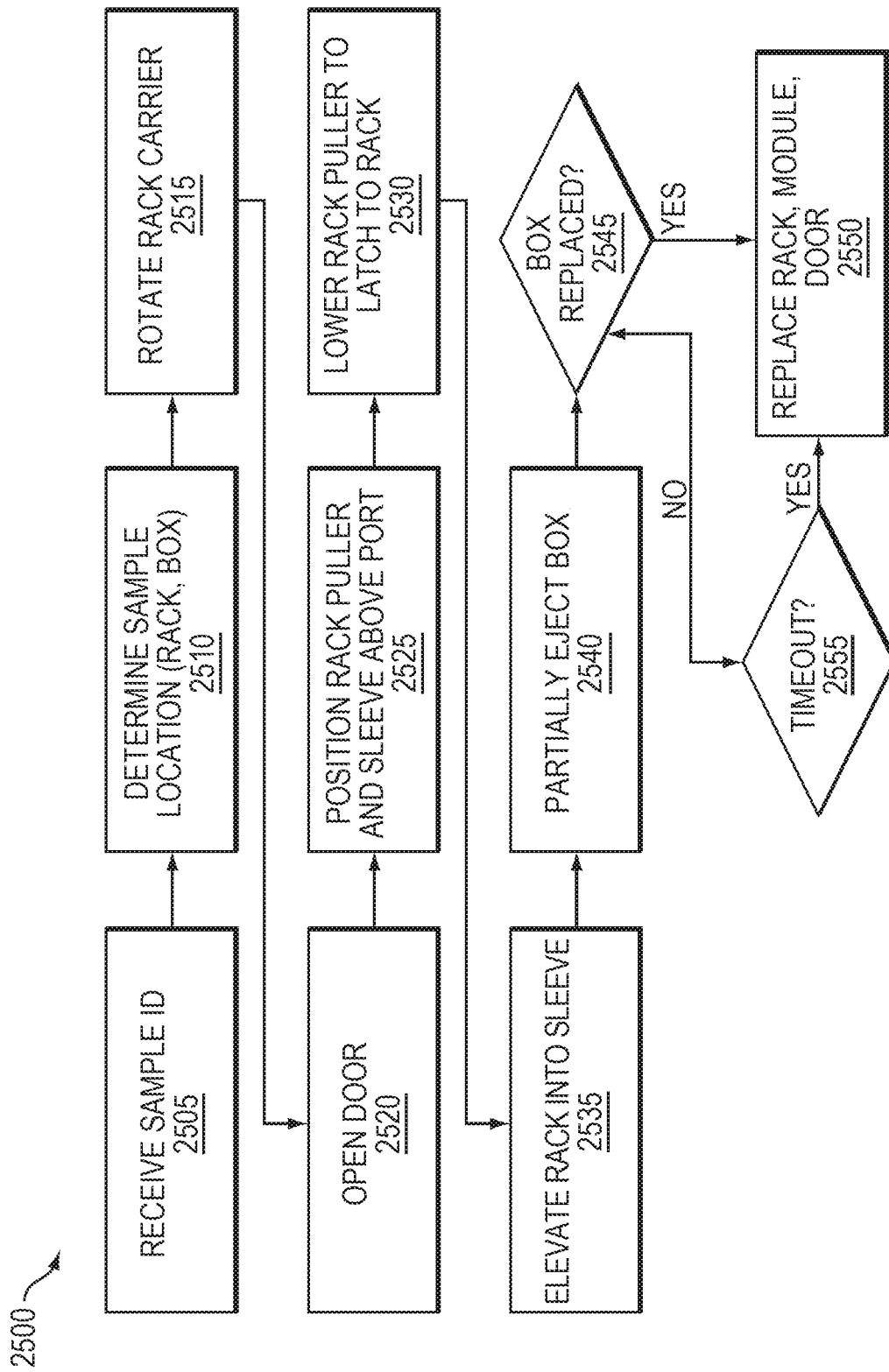
FIG. 25 is a flow diagram of a process of retrieving samples from an automated cryogenic storage system in one embodiment.

FIG. 25 is a flow diagram of a process 2500 of retrieving samples from an automated cryogenic storage system, which may be carried out by either of the systems 100, 2400 described above with reference to FIGS. 1-24. With reference to FIGS. 15 and 24, the controller 180 may receive a sample identifier (ID) for one or more samples to be transferred (2505). For each sample to be transferred, the controller 180 may access the database 185 to determine the present location of the sample, including an address (rack and sample box) of the sample within the freezer 120 (2510). Based on this location, the controller 180 may direct the motor assembly 130 to rotate the rack carrier within the freezer 120 to align the selected rack with the access port 122 (2515). The controller 180 may then direct the motor assembly 130 to open the automated door 140 (2520), and direct the conveyor 170 to position the rack puller 150 and insulating sleeve 160 above the access port 122 and selected rack (2525). Once positioned, the rack puller 150 lowers the gripper assembly 1011 to engage with the selected rack (2530) and elevate the selected rack into the insulating sleeve 160 to a height that aligns the selected sample box with the sleeve port 165 (2535). Prior to or concurrently with elevating the selected rack, the insulating sleeve may be treated with an expellant gas as described above with reference to FIG. 20D.

Once the selected box is aligned with the sleeve port 165, the controller 180 may direct the insulating sleeve 160 to partially eject the box through the sleeve port 165 (2540). The box may then be fully removed, manually, by a user to remove samples from and/or transfer samples to the box. Once it is detected that the box has been replaced to the sleeve port 165 and to the rack (2545), the controller may direct the rack puller 150, motor assembly 130 and conveyor 170 to replace the rack into the freezer 120, reposition the rack puller 150 and insulating sleeve 160, and replace the door 140 to the access port 122, returning the system 100 to a state prior to the transfer operation (2550). Further, if the box is not replaced to the sleeve port 165 within a given time (2555), then a timeout condition may occur, and the system 100 may replace the rack to the freezer 120 without the selected sample box. Doing so may assist in preventing the retrieved rack from reaching an undesirably high temperature while extracted from the freezer 120.

Figure 26A:
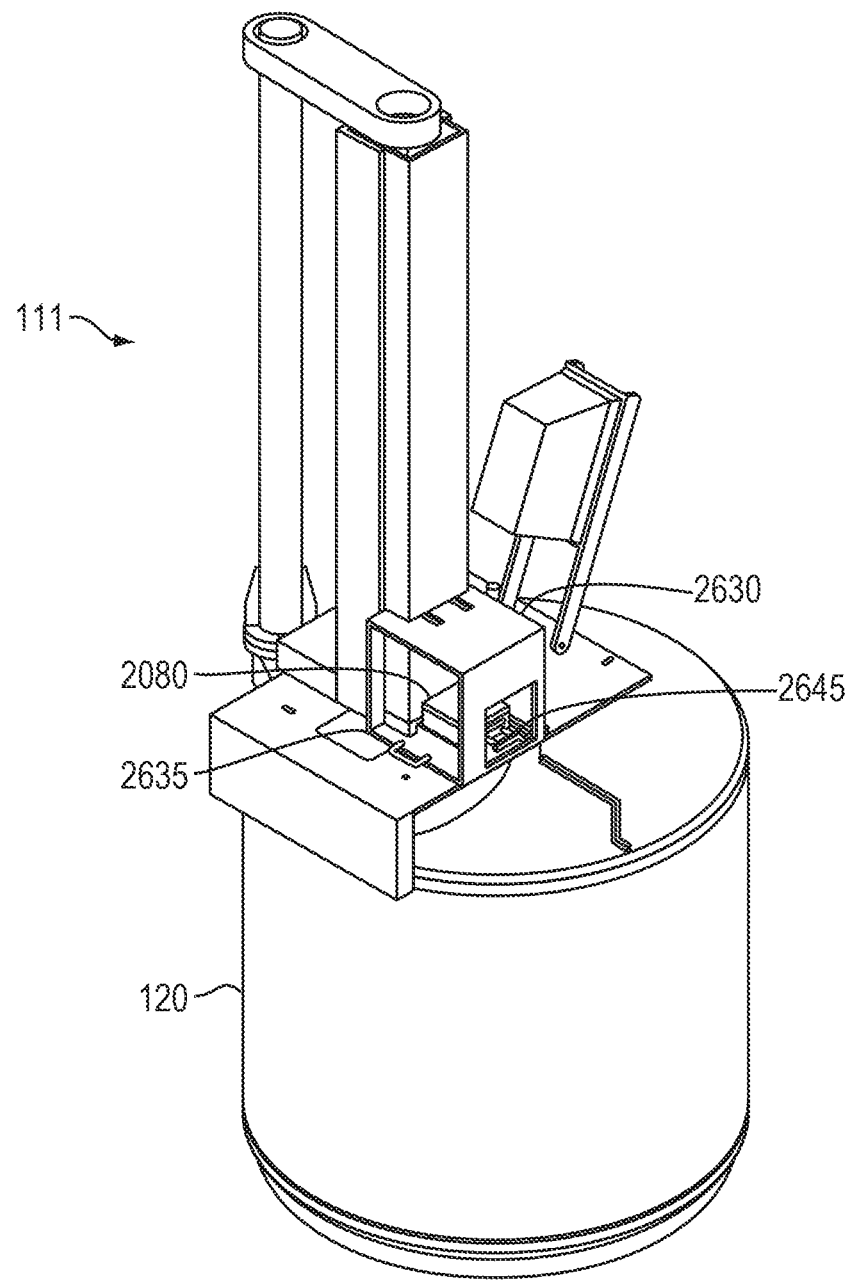
FIGS. 26A-C illustrate automated cryogenic freezers in further embodiments.
Figure 26B:
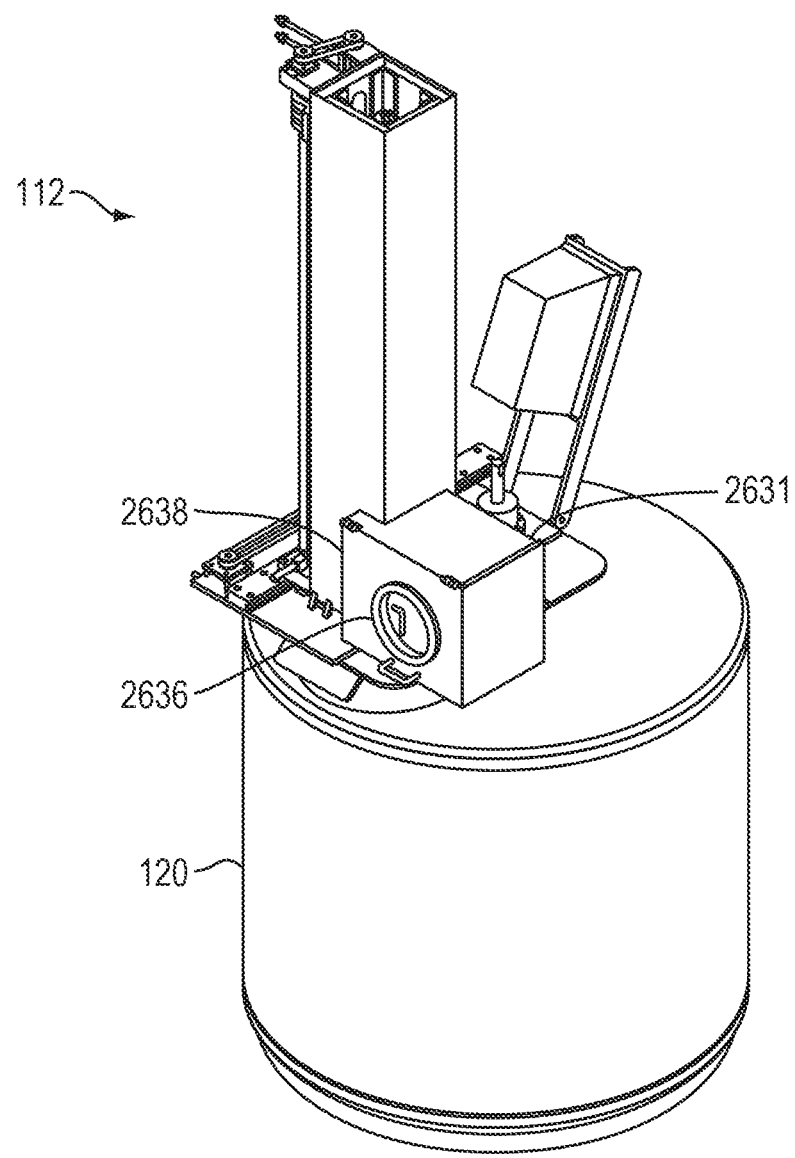
Figure 26C:
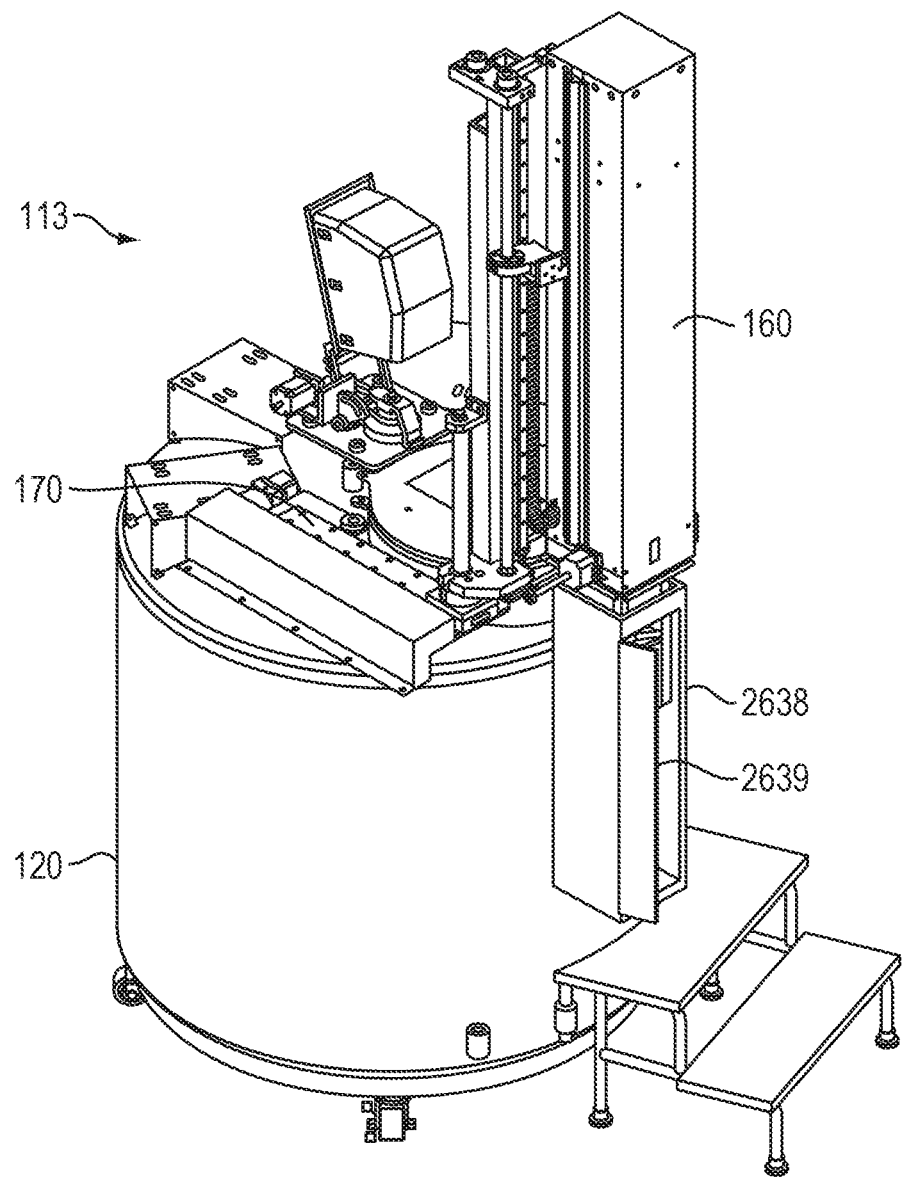

FIGS. 26A-C illustrate automation systems 111, 112, 113 in alternative embodiments. The automation systems 111, 112, 113 may be configured to include some or all of the features of the system 100 and automation system 105 described above with reference to FIGS. 1-25. Further, as shown in FIG. 26A, the automation system 111 may include an antechamber 2630 for housing a sample box 2080 during transfer from and/or to a rack. A box conveyor 2645 may automatically move the sample box 2080 between the rack and the antechamber 2630. Further, an antechamber door 2635 may be manually opened by a user to access the sample box 2080. By providing an antechamber 2630 and box conveyor 2645, the automation system 111 can provide further automation of a sample transfer operation, as well as reduce frost formation on cold sample boxes and/or reduce the quantities of heat and/or moisture entering the freezer.

The automation system 112, shown in FIG. 26B, may include an antechamber 2631 and box conveyor comparable to those of the system 111 of FIG. 26A described above, with the exception that the antechamber door 2638 may include a glove port 2636. The glove port 2636 may enable a user to manipulate samples within a sample box in the antechamber 2631 without opening the door 2638 and thereby reduce frost formation on cold sample boxes.

The automation system 113, shown in FIG. 26C, may include an antechamber 2638 that is adapted to accommodate an entire sample storage rack (e.g., sample storage rack 480 as shown in FIG. 4). In operation, the conveyor 170 may position the sample storage rack (within the insulating sleeve 160) above the antechamber 2638, where it is then lowered into the antechamber 2639. A user may then open the door 2639 to remove and/or replace one or more sample boxes from the sample rack. Alternatively, the user may remove and/or replace the sample storage rack itself. Thus, the automation system 113 provides for bulk loading and unloading of samples to and from the freezer 120.

Figure 27B:
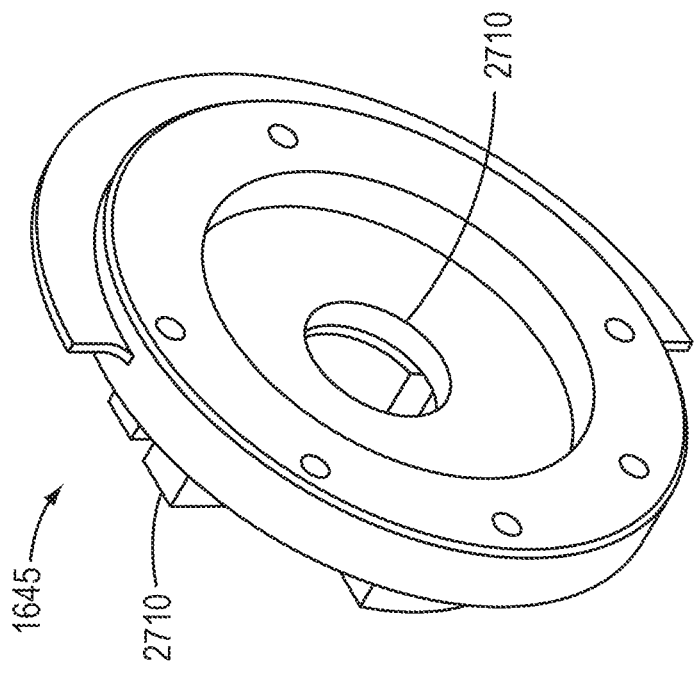
FIGS. 27A-B illustrate a portion of a motor assembly for engaging and locking with a drive shaft in one embodiment.
Figure 27A:
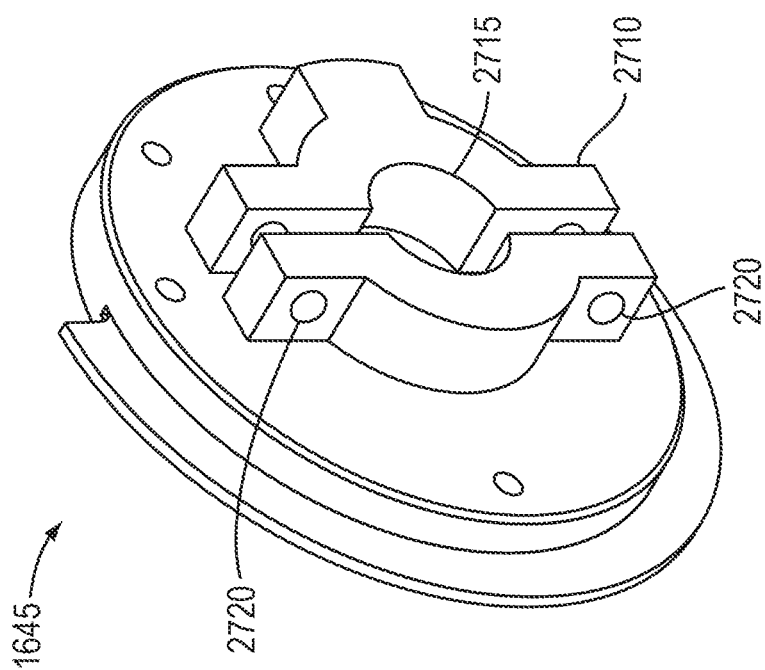

FIGS. 27A-B illustrate a portion of a motor assembly for engaging and locking with a drive shaft. As described above with reference to FIG. 8, to configure the freezer 120 for automated rotation and retrieval of the sample storage racks 480, a motor assembly 130 is attached to the motor mounts 239 and the drive shaft 231. To lift the spherical bearing 733 off of the race 729, the drive shaft 231 may include a threaded exterior end (shown in FIG. 9 as 934). The threaded exterior end of the drive shaft 231 enables rotation of the rack carrier 360 to thread the drive shaft 231 into the motor assembly 130 and lift the spherical bearing 733 off the race 729. Once lifted, the drive shaft 231 may be locked into position in the motor assembly 130 to prevent further threading or de-threading of the drive shaft 231. The motor assembly 130, described above with reference to FIG. 16, includes a locking plate 1650, which engages with the drive shaft 231 to lift and lock the drive shaft into position.

The locking plate 1650 is illustrated in further detail in FIGS. 27A-B. As shown in FIG. 27A, the underside of the locking plate 1650 (i.e., the side facing the freezer cover 121) includes a removable clamp 2710. The clamp 2710 may include a threaded aperture 2715 to engage with the threaded portion of the drive shaft 231 (shown in FIG. 9 as 934). The clamp 2710 can be tightened by adjusted bolts (not shown) positioned at the threaded holes 2720. By tightening the clamp 2710 to a given degree without fully locking the drive shaft 231, the clamp 2710 can provide a torque control over the drive shaft 231. For example, by adjusting the clamp 2710 appropriately, the clamp 2710 will allow the drive shaft 231 to rotate relative to the clamp 2710 when a given amount of torque is applied to the drive shaft 231. By allowing the drive shaft 231 to rotate in response to a threshold torque, damage can be prevented to the drive shaft 231 and components connecting to the drive shaft 231, including the rack carrier 360. An adhesive may also be applied to the inner walls of the clamp aperture to control the threshold torque.

As shown in FIG. 27A, the top side of the locking plate 1650 (i.e., the side that contacts the central gear 1640 as shown in FIG. 16) includes an aperture 2730 aligned with the aperture 2715 of the clamp 2710.

Figure 28A:
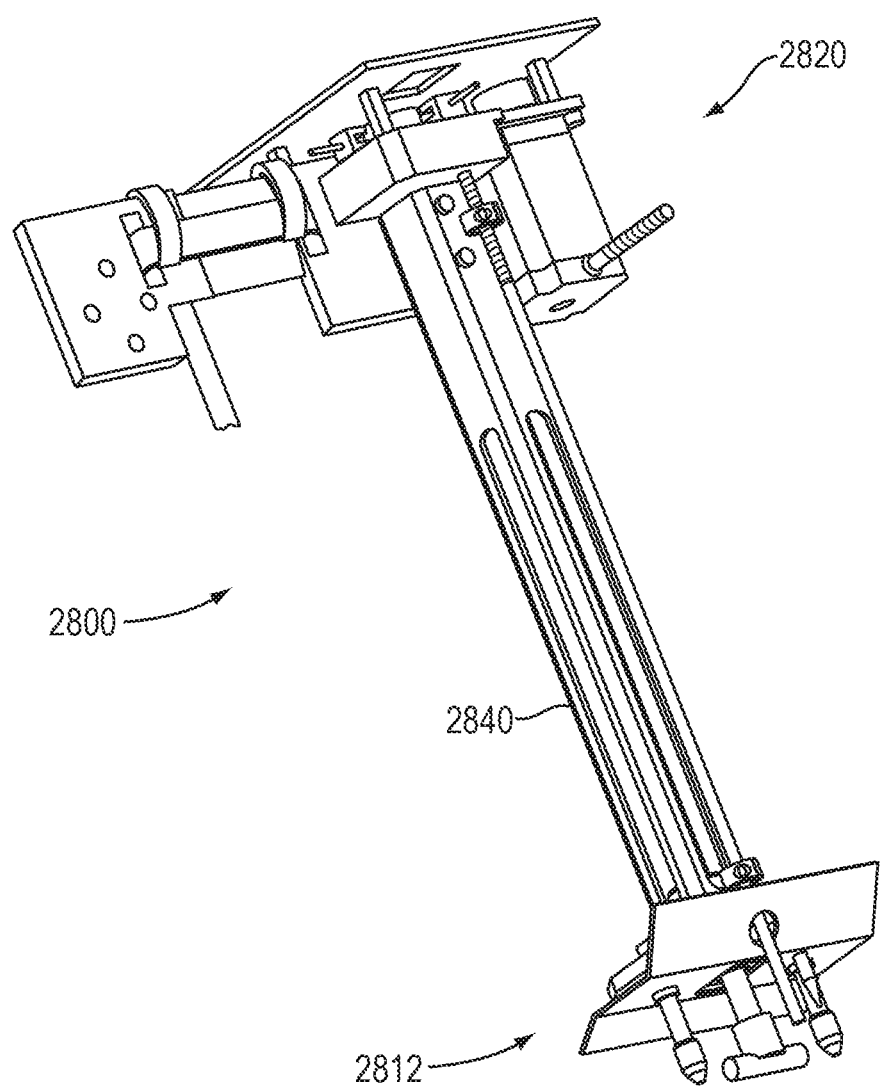
FIGS. 28A-D illustrate a gripper assembly in a further embodiment.

FIGS. 28A-D illustrate a gripping assembly 2800 in a further embodiment. The gripping assembly 2800 may incorporate features of the gripping assembly 1011 described above with reference to FIGS. 11A-B, 12A-B, 13A-C and 19A-B, and may be implemented in place of the gripping assembly 1011 in the embodiments described above. In particular, as shown in FIG. 28A, the gripping assembly 2800 includes a top assembly 2820 for connecting with a bracket 1820 of a rack puller 150 (as shown in FIG. 18), a shaft 2840, and a gripper module 2812 for engaging with a sample rack 480 (as shown in FIG. 11A-B).

As a result of repeatedly entering and exiting a freezer from a warmer (e.g., room-temperature) environment, a gripping assembly may condense moisture at the surfaces of its components, which can freeze to those surfaces while the assembly is in the freezer. Over time, this effect can cause a buildup of ice and frost on the assembly surfaces, which may interfere with the operation of the assembly. The gripping assembly 2800 differs from the gripping assembly 1011 by a number of features as described below. Some of the features, in particular, may assist in preventing a buildup of frost at the gripping assembly 2800, as well as prevent frost from interfering with the operation of the gripping assembly 2800. The gripping assembly 1011 may be modified to incorporate one or more of these features.

Figure 28B:
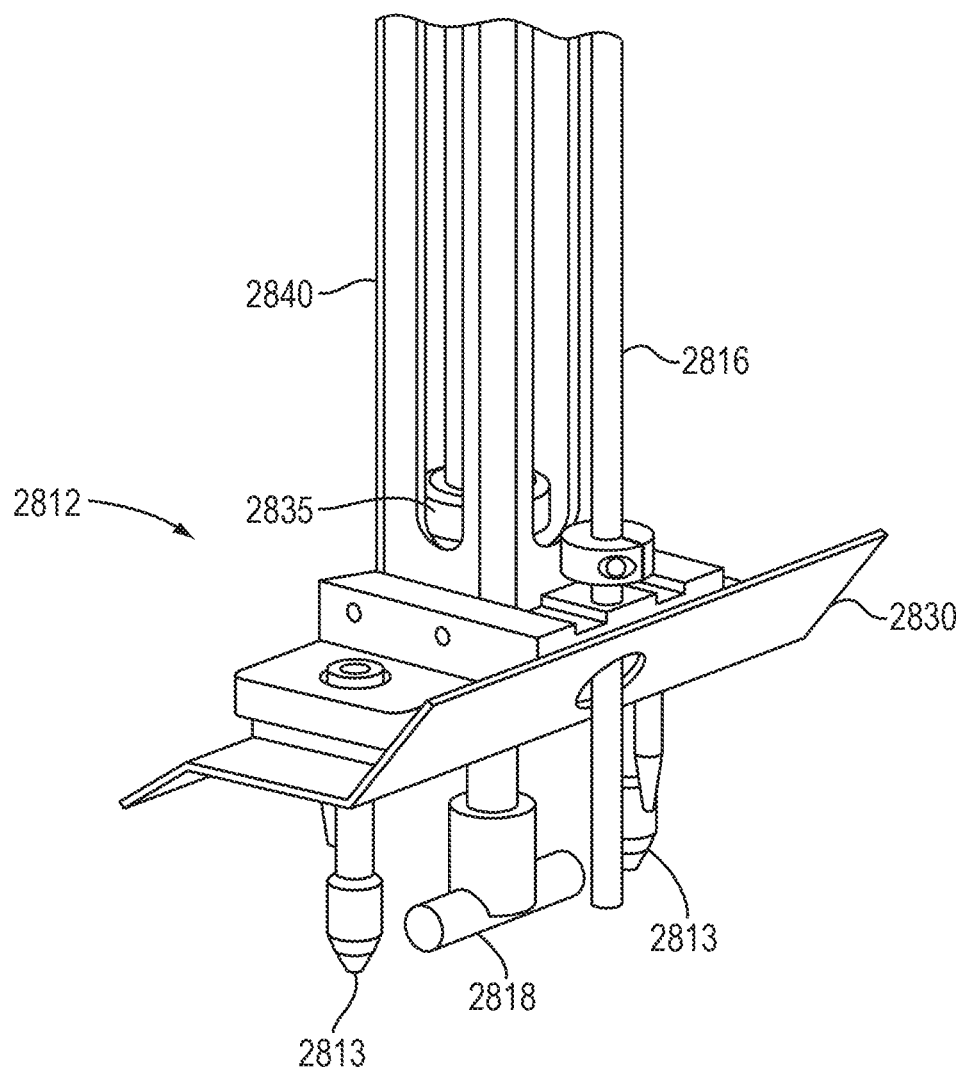

As shown in FIG. 28B, the shaft 2240 comprises a frame having an open interior, in contrast to the solid shape of the shaft of the gripping assembly 1011 described above. Likewise, the locating pins 2813 include a tapered surface toward the underside of the module 2812. By reducing mass and surface area of the shaft 2240, locating pins 2813 and, optionally, other components, the amount of frost that can form on these surfaces is also reduced. Further, a moisture seal 2835 is located within the shaft 2840 and encompasses the rod extending to the T-latch 2018. By creating a seal around the rod, the moisture seal 2835 prevents moisture on the upper portion of the rod from migrating down the rod to the T-latch 2818 and causing a buildup of frost at the T-latch 2818. Rather, a beveled top portion of the moisture seal 2018, also shown in FIG. 28D, assists in directing moisture down the side of the gripper module 2812 to a drip shield 2830.

Figure 28C:
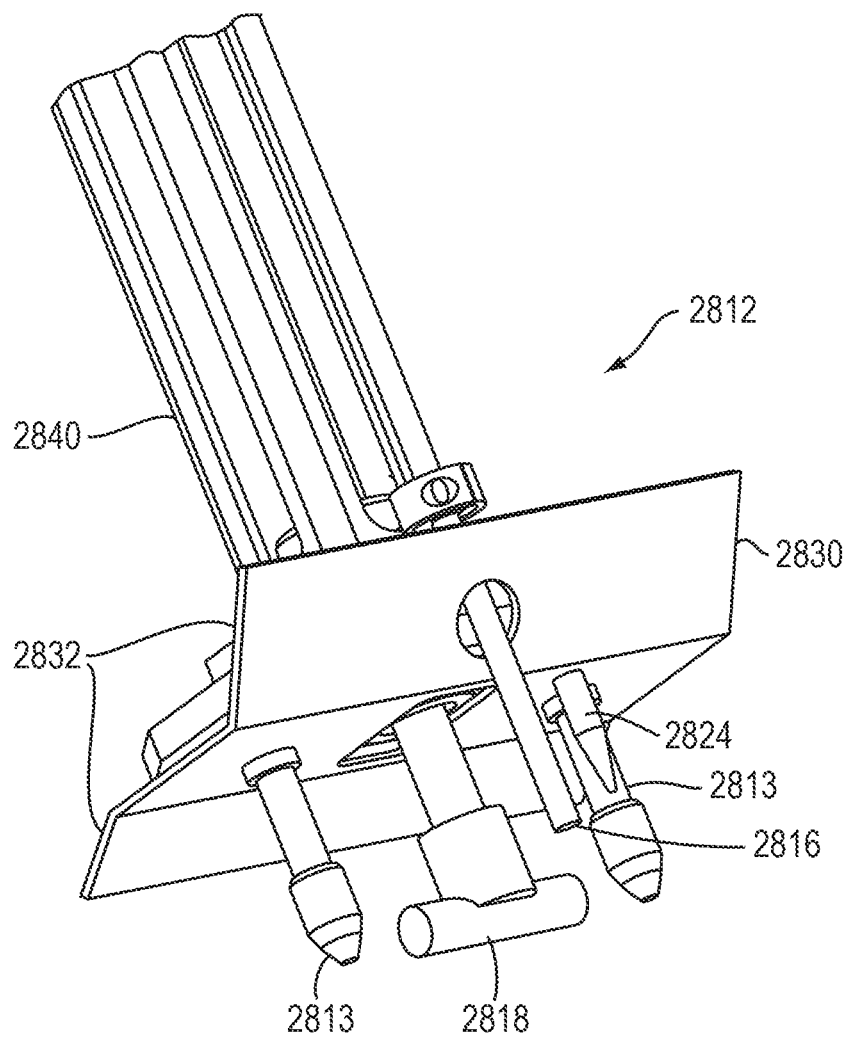
Figure 28D:
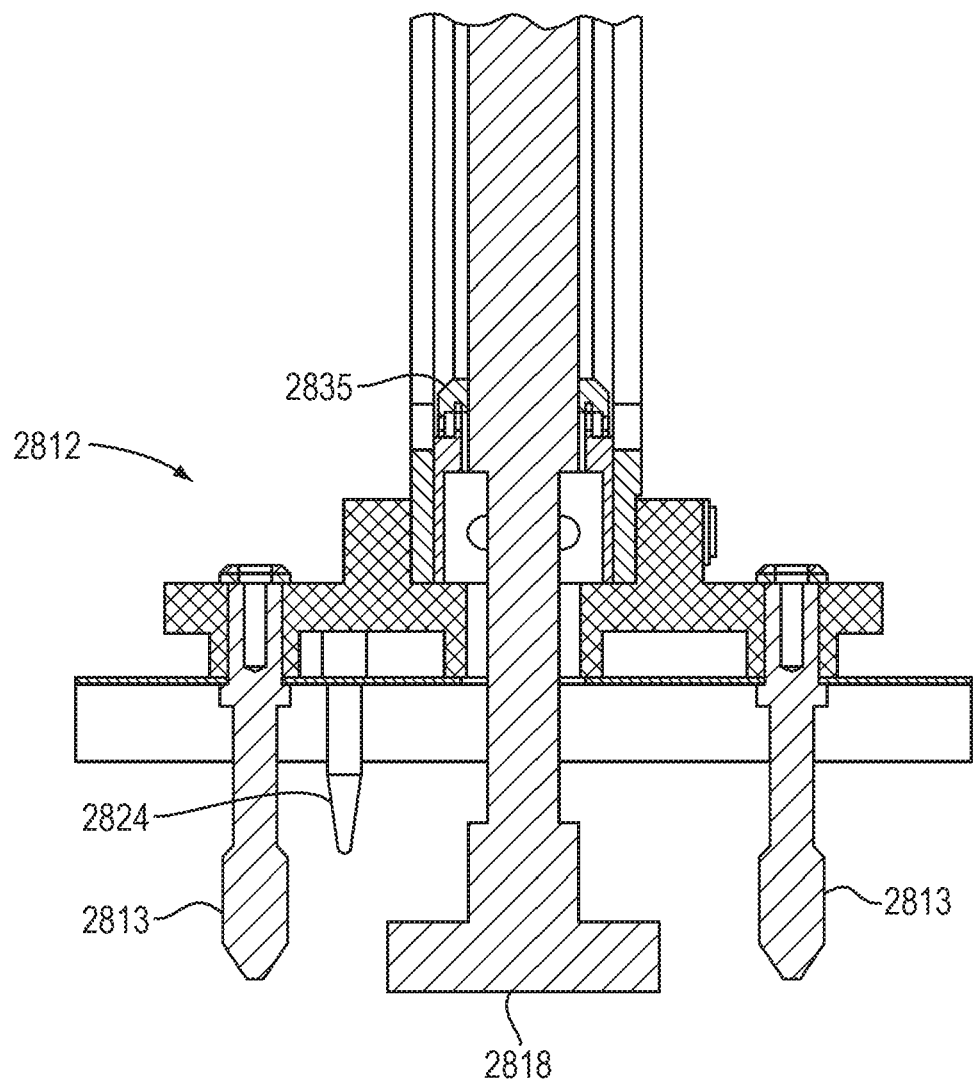

The drip shield 2830, as shown in FIG. 28C, includes leaves 2832, a first of which is angled upward, a second of which is angled downward. As a result, liquid moisture that arrives on the surface of the drip shield 2830 (e.g., from the shaft 2840 or moisture seal 2835) is directed downward toward the lower leaf, where it may drip away from the shield, and away from the components beneath the drip shield 2830, before it can form frost on the module surfaces. The shield 2830 also prevents moisture from dripping onto the top of a rack beneath the gripping module 2812, thereby preventing frost buildup on the top of the rack where it may interfere with the gripping operation. The upper leaf 2832 also includes an aperture for accommodating a sensing rod 2816, which may operate in a manner comparable to the sensing rod 1116 described above with reference to FIGS. 19A-B.

A spacer pin 2824 extends from the bottom surface of the drip shield 2830 and tapers to a contact point. The spacer pin 2824 may extend to a length such that, when the module 2812 engages with a rack, only the spacer pins makes contact with the upper surface of the rack, while the locating pins 2813 and T-Latch 2818 enter corresponding holes in the upper surface of the rack. If a broader surface of the module, which has greater susceptibility to accumulating frost, were to contact the upper surface of a rack, an ice bridge may be formed between the module and the rack, which may prevent the module from detaching from the rack. In contrast, by allowing only the spacer pin 2824 to contact the upper surface of the rack, any ice bridge that may form between the spacer pin 2824 will break when the module 2812 detaches from the rack. Thus, the spacer pin 2824 facilitates detachment between the module 2812 and a rack. Although a single spacer pin 2824 is shown, two or more spacer pins may be implemented. Alternatively, another suitable component, such as an O-ring, a grate, or another length of material may be implemented in place of the spacer pin 2824 to ensure a distance is maintained between the module 2812 and a rack.

In further embodiments, one or more of the spacer pins 2824, locating pins 2813 and T-latch 2818 may be heated continuously, periodically, or before or after insertion in a freezer, in order to remove frost and prevent a buildup of ice or frost. The components may be heated electronically, by convection, or other suitable means. Alternatively, a heat source may be applied to the environment within a sleeve (e.g., insulating sleeve 160), thereby heating the gripping assembly 2800 when located within the sleeve.

Further details of a freezer for use with the invention described herein can be found in the provisional patent application 62/140,160, entitled "Cryogenic Freezer," filed on Mar. 30, 2015, and now filed as a U.S. Utility Application on Mar. 30, 2016, the entirety of which is incorporated herein by reference.

While this invention has been particularly shown and described with references to example embodiments thereof, it will be understood by those skilled in the art that various changes in form and details may be made therein without departing from the scope of the invention encompassed by the appended claims.

What is claimed is:

1. A cryogenic storage system comprising:
   a freezer configured to store a plurality of sample racks in a cryogenic environment, the freezer including a door enabling access to the cryogenic environment through a port at the top portion of the freezer;
   a rack carrier configured to suspend each of the plurality of sample racks by a respective rack top portion, the rack carrier including a rack mount having a plurality of openings, the rack mount suspending each of the plurality of sample racks at a respective one of the plurality of openings; and
   a retrieval system including:
   a drive system mounted to the top portion of the freezer, the drive system being configured to rotate the sample racks to align a selected one of the sample racks with the port;
   an insulating sleeve configured to house the selected one of the sample racks above the port, the insulating sleeve including a sleeve port for enabling a user to access a selected sample box from the selected one of the sample racks; and
   a rack puller, the rack puller being configured to engage the selected one of the sample racks and elevate the selected one of the sample racks through the port and into the insulating sleeve.

2. The system of claim 1, wherein each of the plurality of openings includes a guide extending vertically above a top surface of the rack mount, the guide adapted to center a respective sample rack within the opening as the respective sample rack is lowered through the opening.

3. The system of claim 1, wherein the drive system is configured to engage with a shaft to rotate the rack carrier.

4. The system of claim 3, wherein the shaft is further configured to suspend the rack carrier substantially via the rack mount.

5. The system of claim 1, wherein the rack carrier further includes a plurality of rails each positioned adjacent to a respective one of the plurality of sample racks.

6. The system of claim 1, wherein each of the plurality of racks includes a guideplate at a top portion of the rack, the guideplate including at least one formation for engaging with the rack puller.

7. The system of claim 1, wherein the retrieval system further includes an actuator for automatically opening and closing the door.

8. The system of claim 1, further including a mount configured to mount at least one of the insulating sleeve and rack puller to the top portion of the freezer, the mount further configured to enable the insulating sleeve to be manually repositioned away from the port to enable manual access to the plurality of sample racks.

9. The system of claim 8, wherein the mount further includes a manual release enabling the manual reposition independent of a powered status of the retrieval system.

10. The system of claim 1, wherein the rack puller is further configured to elevate the selected one of the sample racks to a position aligning the selected sample box to the sleeve port.

11. The system of claim 9, wherein the insulating sleeve prevents access to other sample boxes of the selected one of the sample racks when the selected sample box is aligned with the sleeve port.

12. The system of claim 1, wherein the insulating sleeve further includes an inlet to channel an expellant gas into the insulating sleeve.

13. The system of claim 12, wherein the retrieval system is further configured to channel the expellant gas into the insulating sleeve prior to elevating the selected one of the sample racks into the insulating sleeve.

14. The system of claim 1, further including a conveyor configured to automatically move the insulating sleeve and rack puller toward the port.

15. The system of claim 14, wherein the insulating sleeve and rack puller are mounted to the top surface of the freezer by the conveyor.

16. The system of claim 14, wherein the door is further configured to reposition away from the port when the insulating sleeve and rack puller are moved by the conveyor toward the port.

17. The system of claim 1 wherein the freezer is a cryogenic liquid-cooled, vacuum-insulated vessel.

18. The system of claim 1, wherein the door is further configured to reposition away from the port when the insulating sleeve and rack puller are located at the port.

19. The system of claim 1, wherein all of the plurality of sample racks are removable from the rack carrier via operation of the rack puller.

20. A method of cryogenic storage comprising:
storing a plurality of sample racks in a freezer maintaining a cryogenic environment;
suspending each of the plurality of sample racks by a respective rack top portion;
automatically rotating the sample racks to align a selected one of the sample racks with a port through a top portion of the freezer;
automatically opening a door corresponding to the port;
automatically engaging the selected one of the sample racks via a gripping device;
automatically elevating the selected one of the sample racks, via the gripping device, through the port and through an insulating sleeve external to the freezer; and
automatically aligning a selected sample box of the selected one of the sample racks to a sleeve port of the insulating sleeve to enable a user to access the selected sample box.

21. The method of claim 20, further comprising mounting at least one of the insulating sleeve and rack puller to the top portion of the freezer.

22. The method of claim 20, further comprising enabling the insulating sleeve to be manually repositioned away from the port to enable manual access to the plurality of sample racks.

23. The method of claim 20, wherein elevating the selected one of the sample racks includes elevating the selected one of the sample racks to a position aligning the selected sample box to the sleeve port.

24. The method of claim 23, further comprising preventing access to other sample boxes of the selected one of the sample racks when the selected sample box is aligned with the sleeve port.

25. The method of claim 20, further comprising channeling an expellant gas into the insulating sleeve.

26. The method of claim 25, wherein channeling the expellant gas occurs prior to elevating the selected one of the sample racks into the insulating sleeve.

27. The system of claim 20, further comprising automatically moving the insulating sleeve toward the port.

* * * * *